US008003345B2

(12) United States Patent
Fesenko et al.

(10) Patent No.: US 8,003,345 B2
(45) Date of Patent: Aug. 23, 2011

(54) ANTIOXIDANT PHARMACEUTICAL COMPOUND, METHOD FOR PRODUCING POLYPEPTIDE AND METHOD OF CURE

(75) Inventors: Evgeny Evgenyevich Fesenko, Puschino (RU); Vladimir Ivanovich Novoselov, Puschino (RU); Vadim Alekseevich Yanin, Puschino (RU); Valery Mikhaylovich Lipkin, Moscow (RU); Tatyana Maratovna Shuvaeva, Moscow (RU)

(73) Assignee: Institute of Cell Biophysics Russian Academy of Sciences, Moskovskaya Oblast (RU)

( * ) Notice: Subject to any disclaimer, the term of this patent is extended or adjusted under 35 U.S.C. 154(b) by 304 days.

(21) Appl. No.: 10/534,238

(22) PCT Filed: Nov. 5, 2003

(86) PCT No.: PCT/RU03/00473
§ 371 (c)(1),
(2), (4) Date: Dec. 2, 2005

(87) PCT Pub. No.: WO2004/043485
PCT Pub. Date: May 27, 2004

(65) Prior Publication Data
US 2006/0147440 A1    Jul. 6, 2006

(30) Foreign Application Priority Data

Nov. 10, 2002  (RU) ................................ 2002129774
Jul. 29, 2003  (RU) ................................ 2003123534

(51) Int. Cl.
C12N 15/00    (2006.01)
C07H 21/02    (2006.01)
C12P 21/06    (2006.01)

(52) U.S. Cl. ..................... 435/69.1; 536/23.1; 435/320.1
(58) Field of Classification Search .................. 536/23.1; 435/69.1, 252.3, 320.1; 530/350
See application file for complete search history.

(56) References Cited

U.S. PATENT DOCUMENTS

| 2002/0168353 | A1 | 11/2002 | Lynn et al. |
| 2003/0124137 | A1 | 7/2003 | Dalton et al. |
| 2003/0186839 | A1 | 10/2003 | Awaya et al. |
| 2007/0042425 | A1 | 2/2007 | Hochstrasser et al. |
| 2007/0196844 | A1 | 8/2007 | Pestlin et al. |
| 2007/0292406 | A1 | 12/2007 | Kang et al. |

FOREIGN PATENT DOCUMENTS

| EP | 1394182 A1 | 3/2004 |
| FR | 2798672 | 3/2001 |
| JP | 2008275413 A | 11/2008 |
| KR | 20050046916 A | 5/2005 |
| KR | 20050052754 A | 6/2005 |
| KR | 20060020140 A | 3/2006 |
| RU | 2250262 | 3/2005 |
| RU | 2280448 | 7/2006 |
| WO | 98/43666 | 8/1998 |
| WO | 2007/140976 A2 | 12/2007 |
| WO | 2008/036835 A2 | 3/2008 |

OTHER PUBLICATIONS

Fujii et al. "Augmented expression of peroxiredoxin VI in rat lung and kidney after birth implies an antioxidative role," Eur. J. Biochem., vol. 268, pp. 218-224, 2001.*
Kang et al. "Characterization of a Mammalian Peroxiredoxin that contains one conserved Cysteine," The J. of Biol. Chem., vol. 273, No. 11, pp. 6303-6311, Mar. 13, 1998.*
Kang et al. "Peroxiredoxin-6, 1-Cys peroxiredoxin," SEQ ID No. 2 alignment result 1, Accession No. PRDX6_HUMAN, Database: UniProt_8.4.*
SEQ ID No. 2 alignment result 10, Accession No. PRDX6_MOUSE, Database: UniProt_8.4.*
Espacenet English Abstract of FR 2798672 B1, 2003.
Espacenet English Abstract of JP 2008275413 A, 2008.
Kumin A. et al. Peroxiredoxin 6 is a Potent Cytoprotective Enzyme in the Epidermis. The American Journal of Pathology, vol. 169, No. 4, Oct. 2006, 1194-1205.
A. Nekrasov et all The Novel Approach to the Protein Design: Active Truncated Forms of Human 1-CYS Peroxiredoxin. J. of Biomolec. Structure & Dynamics, V.24 No. 5 (2007). http//www.jbsdonline.com.
Trudel S. et al. Peroxiredoxin 6 Fails to Limit Phospholipid Peroxidation in Lung from C/Tr-Knockout Mice Subjected to Oxidative Challenge. Jun. 29, 2009. (http://www.plosone.Org/article/info:doi%2F10.1371 %2Fiournal.pone.0006075).
Espacenet Bibliographic data of KR 20060020140 A, 2006.
Espacenet Bibliographic data of KR 20050046916 A, 2005.
Espacenet English Abstract of KR 20010083976 A, 2001.
Espacenet English Abstract of RU 2250262, 2005.
W. Lee et al. Human Peroxiredoxin 1 and 2 Are Not Duplicate Proteins: The Unique Presence of CYS83 in Prx1 Underscores the Structural and Functional Differences Between Prx1 and Prx2 J. Biol. Chem. 2007.

* cited by examiner

*Primary Examiner* — Maryam Monshipouri
(74) *Attorney, Agent, or Firm* — Ladas & Parry LLP

(57) ABSTRACT

The invention relates to a pharmaceutical compound for antioxidant protection of cells, tissues and entire organism against hyperproduction of fee radicals. The inventive compound comprises an effective quantity of at least one antioxidant in the form of a main acting component. Said antioxidant is selected from a group consisting peroxiredoxine, a fragment thereof, dihydrolipoic acid and the combinations thereof with acceptable pharmaceutical additives. The inventive method for preventing and curing mammals consists in contacting the effective quantity of the compound with intercellular space of tissue, organ and entire mammal organism. Low toxicity of the compound makes it possible to increase the efficiency of treatment of multifactor actions on an organism, for example radiation, thermal, chemical burn, wounds and hurts as a result of disasters and fires.

9 Claims, 11 Drawing Sheets

A

B

C

A

B

C

A

B

C

A

B

Figure 1:
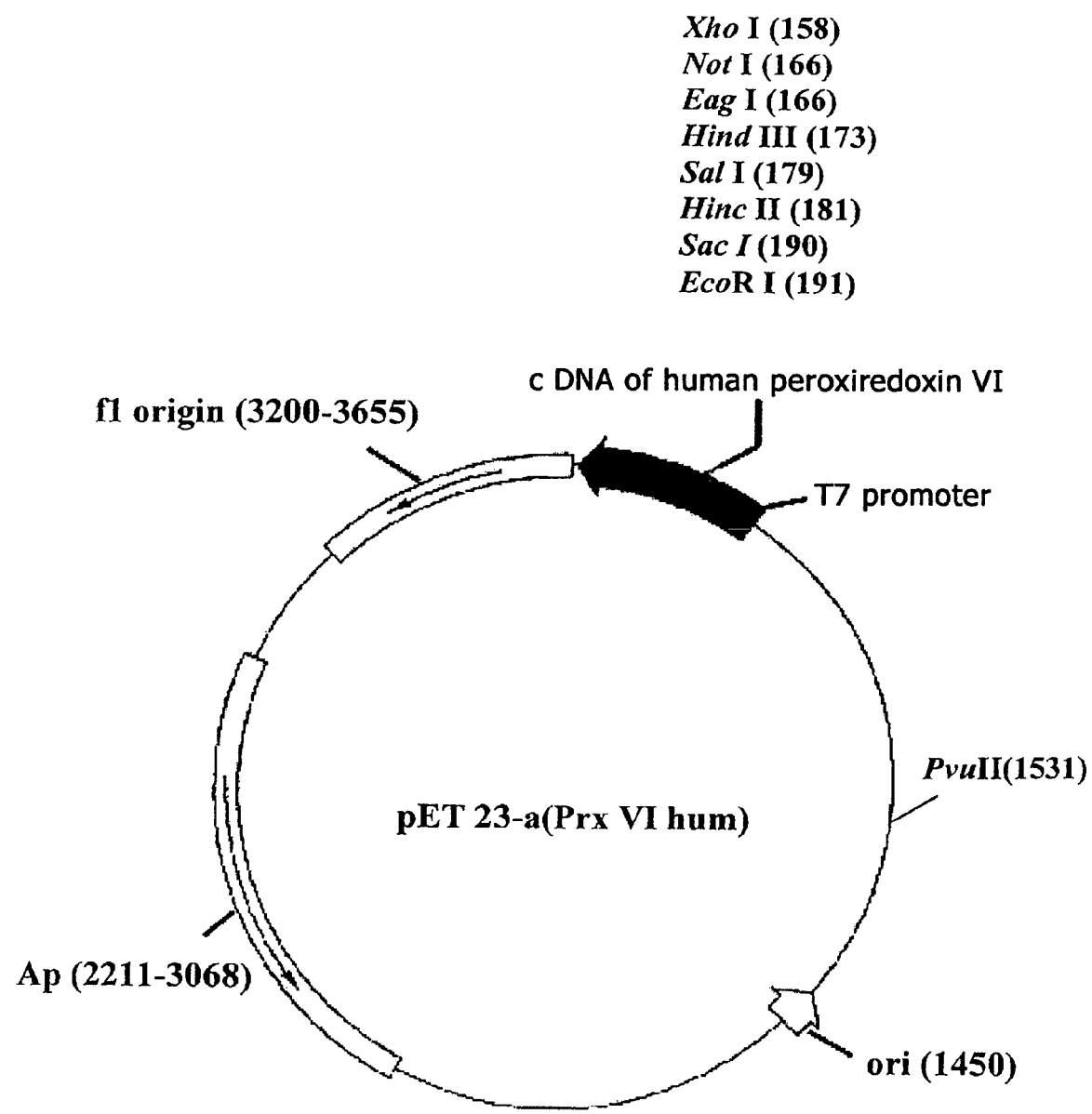

SEQUENCE LISTING

<160> NUMBER OF SEQ ID NOS: 8

<210> SEQ ID NO 1
<211> LENGTH: 715
<212> TYPE: DNA
<213> ORGANISM: Homo sapiens
<220> FEATURE:
<221> NAME/KEY: CDS
<222> LOCATION: (44)..(715)

<400> SEQUENCE: 1

```
cggttgcttg ctgtcccagc ggcgcccct catcaccgtc gcc atg ccc gga ggt         55
                                            Met Pro Gly Gly
                                              1 ctg ctt ctc ggg gac gtg gct ccc aac ttt gag gcc aat acc acc gtc        103
Leu Leu Leu Gly Asp Val Ala Pro Asn Phe Glu Ala Asn Thr Thr Val
```

```
             5                  10                  15                  20
ggc cgc atc cgt ttc cac gac ttt ctg gga gac tca tgg ggc att ctc      151
Gly Arg Ile Arg Phe His Asp Phe Leu Gly Asp Ser Trp Gly Ile Leu
                     25                  30                  35 ttc tcc cac cct cgg gac ttt acc cca gtg tgc acc aca gag ctt ggc      199
Phe Ser His Pro Arg Asp Phe Thr Pro Val Cys Thr Thr Glu Leu Gly
             40                  45                  50 aga gct gca aag ctg gca cca gaa ttt gcc aag agg aat gtt aag ttg      247
Arg Ala Ala Lys Leu Ala Pro Glu Phe Ala Lys Arg Asn Val Lys Leu
                     55                  60                  65 att gcc ctt tca ata gac agt gtt gag gac cat ctt gcc tgg agc aag      295
Ile Ala Leu Ser Ile Asp Ser Val Glu Asp His Leu Ala Trp Ser Lys
         70                  75                  80 gat atc aat gct tac aat tgt gaa gag ccc aca gaa aag tta cct ttt      343
Asp Ile Asn Ala Tyr Asn Cys Glu Glu Pro Thr Glu Lys Leu Pro Phe
85                  90                  95                 100 ccc atc atc gat gat agg aat cgg gag ctt gcc atc ctg ttg ggc atg      391
Pro Ile Ile Asp Asp Arg Asn Arg Glu Leu Ala Ile Leu Leu Gly Met
                 105                 110                 115 ctg gat cca gca gag aag gat gaa aag ggc atg cct gtg aca gct cgt      439
Leu Asp Pro Ala Glu Lys Asp Glu Lys Gly Met Pro Val Thr Ala Arg
             120                 125                 130 gtg gtg ttt gtt ttt ggt cct gat aag aag ctg aag ctg tct atc ctc      487
Val Val Phe Val Phe Gly Pro Asp Lys Lys Leu Lys Leu Ser Ile Leu
                     135                 140                 145 tac cca gct acc act ggc agg aac ttt gat gag att ctc agg gta gtc      535
Tyr Pro Ala Thr Thr Gly Arg Asn Phe Asp Glu Ile Leu Arg Val Val
             150                 155                 160 atc tct ctc cag ctg aca gca gaa aaa agg gtt gcc acc cca gtt gat      583
Ile Ser Leu Gln Leu Thr Ala Glu Lys Arg Val Ala Thr Pro Val Asp
165                 170                 175                 180 tgg aag gat ggg gat agt gtg atg gtc ctt cca acc atc cct gaa gaa      631
Trp Lys Asp Gly Asp Ser Val Met Val Leu Pro Thr Ile Pro Glu Glu
                 185                 190                 195 gaa gcc aaa aaa ctt ttc ccg aaa gga gtc ttc acc aaa gag ctc cca      679
Glu Ala Lys Lys Leu Phe Pro Lys Gly Val Phe Thr Lys Glu Leu Pro
             200                 205                 210 tct ggc aag aaa tac ctc cgc tac aca ccc cag cct                      715
Ser Gly Lys Lys Tyr Leu Arg Tyr Thr Pro Gln Pro
         215                 220

<210> SEQ ID NO 2
<211> LENGTH: 224
<212> TYPE: PRT
<213> ORGANISM: Homo sapiens

<400> SEQUENCE: 2

Met Pro Gly Gly Leu Leu Gly Asp Val Ala Pro Asn Phe Glu Ala
1               5                   10                  15

Asn Thr Thr Val Gly Arg Ile Arg Phe His Asp Phe Leu Gly Asp Ser
                 20                  25                  30

Trp Gly Ile Leu Phe Ser His Pro Arg Asp Phe Thr Pro Val Cys Thr
             35                  40                  45

Thr Glu Leu Gly Arg Ala Ala Lys Leu Ala Pro Glu Phe Ala Lys Arg
         50                  55                  60

Asn Val Lys Leu Ile Ala Leu Ser Ile Asp Ser Val Glu Asp His Leu
65                  70                  75                  80

Ala Trp Ser Lys Asp Ile Asn Ala Tyr Asn Cys Glu Glu Pro Thr Glu
                 85                  90                  95
```

```
                Lys Leu Pro Phe Pro Ile Ile Asp Asp Arg Asn Arg Glu Leu Ala Ile
                                100                 105                 110

Leu Leu Gly Met Leu Asp Pro Ala Glu Lys Asp Glu Lys Gly Met Pro
                            115                 120                 125

Val Thr Ala Arg Val Val Phe Val Phe Gly Pro Asp Lys Lys Leu Lys
                        130                 135                 140

Leu Ser Ile Leu Tyr Pro Ala Thr Thr Gly Arg Asn Phe Asp Glu Ile
                145                 150                 155                 160

Leu Arg Val Val Ile Ser Leu Gln Leu Thr Ala Glu Lys Arg Val Ala
                                165                 170                 175

Thr Pro Val Asp Trp Lys Asp Gly Asp Ser Val Met Val Leu Pro Thr
                            180                 185                 190

Ile Pro Glu Glu Glu Ala Lys Lys Leu Phe Pro Lys Gly Val Phe Thr
                        195                 200                 205

Lys Glu Leu Pro Ser Gly Lys Lys Tyr Leu Arg Tyr Thr Pro Gln Pro
                210                 215                 220

<210> SEQ ID NO 3
<211> LENGTH: 574
<212> TYPE: DNA
<213> ORGANISM: Homo sapiens
<220> FEATURE:
<221> NAME/KEY: CDS
<222> LOCATION: (44)..(574)

<400> SEQUENCE: 3
cggttgcttg ctgtcccagc ggcgccccct catcaccgtc gcc atg ccc gga ggt          55
                                            Met Pro Gly Gly
                                             1 ctg ctt ctc ggg gac gtg gct ccc aac ttt gag gcc aat acc acc gtc         103
Leu Leu Leu Gly Asp Val Ala Pro Asn Phe Glu Ala Asn Thr Thr Val
 5                  10                  15                  20 ggc cgc atc cgt ttc cac gac ttt ctg gga gac tca tgg ggc att ctc         151
Gly Arg Ile Arg Phe His Asp Phe Leu Gly Asp Ser Trp Gly Ile Leu
                 25                  30                  35 ttc tcc cac cct cgg gac ttt acc cca gtg tgc acc aca gag ctt ggc         199
Phe Ser His Pro Arg Asp Phe Thr Pro Val Cys Thr Thr Glu Leu Gly
             40                  45                  50 aga gct gca aag ctg gca cca gaa ttt gcc aag agg aat gtt aag ttg         247
Arg Ala Ala Lys Leu Ala Pro Glu Phe Ala Lys Arg Asn Val Lys Leu
         55                  60                  65 att gcc ctt tca ata gac agt gtt gag gac cat ctt gcc tgg agc aag         295
Ile Ala Leu Ser Ile Asp Ser Val Glu Asp His Leu Ala Trp Ser Lys
     70                  75                  80 gat atc aat gct tac aat tgt gaa gag ccc aca gaa aag tta cct ttt         343
Asp Ile Asn Ala Tyr Asn Cys Glu Glu Pro Thr Glu Lys Leu Pro Phe
 85                  90                  95                 100 ccc atc atc gat gat agg aat cgg gag ctt gcc atc ctg ttg ggc atg         391
Pro Ile Ile Asp Asp Arg Asn Arg Glu Leu Ala Ile Leu Leu Gly Met
                 105                 110                 115 ctg gat cca gca gag aag gat gaa aag ggc atg cct gtg aca gct cgt         439
Leu Asp Pro Ala Glu Lys Asp Glu Lys Gly Met Pro Val Thr Ala Arg
             120                 125                 130 gtg gtg ttt gtt ttt ggt cct gat aag aag ctg aag ctg tct atc ctc         487
Val Val Phe Val Phe Gly Pro Asp Lys Lys Leu Lys Leu Ser Ile Leu
         135                 140                 145 tac cca gct acc act ggc agg aac ttt gat gag att ctc agg gta gtc         535
Tyr Pro Ala Thr Thr Gly Arg Asn Phe Asp Glu Ile Leu Arg Val Val
     150                 155                 160 atc tct ctc cag ctg aca gca gaa aaa agg gtt gcc acc                     574
Ile Ser Leu Gln Leu Thr Ala Glu Lys Arg Val Ala Thr
 165                 170                 175
```

```
Ile Ser Leu Gln Leu Thr Ala Glu Lys Arg Val Ala Thr
165                 170                 175

<210> SEQ ID NO 4
<211> LENGTH: 177
<212> TYPE: PRT
<213> ORGANISM: Homo sapiens

<400> SEQUENCE: 4

Met Pro Gly Gly Leu Leu Gly Asp Val Ala Pro Asn Phe Glu Ala
1               5                   10                  15

Asn Thr Thr Val Gly Arg Ile Arg Phe His Asp Phe Leu Gly Asp Ser
                20                  25                  30

Trp Gly Ile Leu Phe Ser His Pro Arg Asp Phe Thr Pro Val Cys Thr
            35                  40                  45

Thr Glu Leu Gly Arg Ala Ala Lys Leu Ala Pro Glu Phe Ala Lys Arg
    50                  55                  60

Asn Val Lys Leu Ile Ala Leu Ser Ile Asp Ser Val Glu Asp His Leu
65                  70                  75                  80

Ala Trp Ser Lys Asp Ile Asn Ala Tyr Asn Cys Glu Glu Pro Thr Glu
                85                  90                  95

Lys Leu Pro Phe Pro Ile Ile Asp Asp Arg Asn Arg Glu Leu Ala Ile
                100                 105                 110

Leu Leu Gly Met Leu Asp Pro Ala Glu Lys Asp Glu Lys Gly Met Pro
            115                 120                 125

Val Thr Ala Arg Val Val Phe Val Phe Gly Pro Asp Lys Lys Leu Lys
    130                 135                 140

Leu Ser Ile Leu Tyr Pro Ala Thr Thr Gly Arg Asn Phe Asp Glu Ile
145                 150                 155                 160

Leu Arg Val Val Ile Ser Leu Gln Leu Thr Ala Glu Lys Arg Val Ala
                165                 170                 175

Thr

<210> SEQ ID NO 5
<211> LENGTH: 23
<212> TYPE: DNA
<213> ORGANISM: Artificial Sequence
<220> FEATURE:
<223> OTHER INFORMATION: Artificially generated

<400> SEQUENCE: 5
atcaccgtcc atatgcccgg agg                                              23

<210> SEQ ID NO 6
<211> LENGTH: 25
<212> TYPE: DNA
<213> ORGANISM: Artificial Sequence
<220> FEATURE:
<223> OTHER INFORMATION: Artificially generated

<400> SEQUENCE: 6
ccagaattct taaggctggg gtgtg                                            25

<210> SEQ ID NO 7
<211> LENGTH: 27
<212> TYPE: DNA
<213> ORGANISM: artificial Sequence
<220> FEATURE:
<223> OTHER INFORMATION: Artificially generated

<400> SEQUENCE: 7
```

```
gcgaaattaa tacgactcac tataggg                                        27

<210> SEQ ID NO 8
<211> LENGTH: 27
<212> TYPE: DNA
<213> ORGANISM: Artificial Sequence
<220> FEATURE:
<223> OTHER INFORMATION: Artificially generated

<400> SEQUENCE: 8
ccatccttcg aattcaactt aggtggc                                        27
```

ANTIOXIDANT PHARMACEUTICAL COMPOUND, METHOD FOR PRODUCING POLYPEPTIDE AND METHOD OF CURE

This application is the National Stage entry of PCT/RU03/00473, filed Nov. 5, 2003, which claims priority to Russian application Numbers: 2002129774 and 2003123534, filed Nov. 10, 2002 and Jul. 29, 2003, respectively.

FIELD OF THE ART

The present invention relates to the field of medicine, biotechnology and genetic engineering and can be used in producing an antioxidant preparation peroxiredoxin and fragments thereof as components of a pharmaceutical composition intended for the prevention and/or treatment of pathologies which are partially or fully caused by an imbalance between oxidation and reduction processes in mammalian organisms.

PRIOR ART

An antioxidant protection system existing in mammalian organisms is an important link that provides dynamic constancy of the composition of the cells and liquid media of organism, including blood and lymph. Antioxidant intracellular enzyme systems counteract oxidative stress and neutralize active forms of oxygen. Respiratory organs, which have an effective endogenous antioxidant protection in the respiratory, hold an important place in this respect (Bauer V. et al., 1999).

Under the effect of oxidative stress cell looses regulatory functions, and this affects the functional properties of enzymes, proteins and ribonucleic acids. This, ultimately, may lead to the origination of avalanche-like processes of cell death.

The balance between the formation of active forms of oxygen and the antioxidant protection is disturbed as a result of numerous diseases or due to the action of endogenous and/or exogenous factors on the organism. Balance disturbance is induced in the case of: a) bacterial or viral infection, b) action of thermal and/or chemical factors (burn, frostbite), c) mechanical injuries (wounds, fractures, concussions), d) exposure to ionizing and non-ionizing radiation.

Development of effective medicaments which contribute to the prevention or treatment of diseases accompanied by hyperproduction of free radicals is an important task of pharmacology.

Usually the term "antioxidant" is used to denote a substance which lowers the level or prevents the formation of active radicals or active forms of oxygen.

There is known a wide range of diseases, in treating which antioxidant preparations have confirmed their effectiveness (Babish J. G. et al., PCT Appl. WO0230419, 2002). To such diseases there belong: a) pulmonary diseases, b) hepatic diseases, c) kidney diseases, d) diseases of the intestinal tract, e) diseases of the immune system, f) diseases of the nervous system, g) ocular diseases, h) inflammatory processes, i) cardiac diseases, j) virus infections, e.g., AIDS and others.

There exist several approaches in search of antioxidants which enhance the effectiveness of treating or preventing diseases induced by both exogenous and endogenous factors.

It is known to use low-molecular hydrophilic and hydrophobic antioxidants, such as α-tocopherol, ubiquinones, N-acetylcysteine, glutathione (Glissen A. et al., 1998; Kelly F. J., 1999; Tabot O. et al., U.S. Pat. No. 6,187,743, 2001). It is known to use low -molecular peptides which have antioxidant activity (McLean et al., U.S. Pat. No. 5,683,982, 1997). A common disadvantage in using low-molecular antioxidants is that they have rather low antioxidant activity and are not effective in heavy pathologies.

Another approach is associated with the use of antioxidants having a high degree of antioxidant activity.

It is known to use thioredoxin which induces the synthesis of cellular antioxidant MnSOD in treating lung epithelial cells (White K. et al., U.S. Pat. No. 5,985,261, 1999) or to use a recombinant SOD for preventing lung diseases (Davis J. M. et al., 1993). A common disadvantage of using the known high-molecular enzymes is a narrow range of their action. Examples of combined application of low-molecular and high-molecular antioxidants are known, for instance, for protecting cells against the action of free radicals (Hellstrand K. et al., 2000) or for treating particular diseases, e.g., vascular diseases (Vita J. A. et al., 2001).

It should be pointed out that widely used antioxidants, such as α-tocopherol, carotenoids, flavonoids, probucol, interact mainly with radicals localized in the hydrophobic zone of cellular membranes and lipoproteins. At the same time, hyperproduction of free radicals in the first phase of inflammatory diseases is localized in an aqueous phase where maximum activity is displayed by hydrophilic interceptors of active forms of oxygen.

At present a new class of naturally occurring antioxidants is discovered, which are readily soluble in water, are noted for a wide range of antioxidant activity, and have been experimentally investigated in vitro. To such class there belong thiol-specific antioxidants or peroxiredoxins which are capable of neutralizing both organic and inorganic compounds in a wide range of their concentration (Chae H. Z. et al., 1994; McConingle S. et al., 1998). From in vitro experiments it is known that many of peroxiredoxins take part in the cell proliferation process (Prosperi M. T. et al., 1993; Pesenrko I. V. et al., 1998; Novoselov S. V. et al., 1999).

Publications are known, in which the role of peroxiredoxins in cells was studied in cells in dysfunctions caused by: atherosclerosis (Butterfield L. H., 1999), cancer (Chung Y. M. et al., 2001; Kinnula V. L. et al., 2002), nervous diseases (Kim S. H. et al., 2001), pulmonary diseases (Das K. C. et al., 2001; Kim H. S. et al., 2002), kidney diseases (Fujii T., 2001), skin diseases (Lee S. C. et al., 2000), ionizing radiation (Park S. H. et al., 2000).

Pointing out to the important role of the peroxiredoxin synthesis in cells in response to oxidant stress, the authors of the publications proposed to increase the content of different types of peroxiredoxins inside the cell.

A method of treatment is known, based on increasing the peroxiredoxin level in the cell with the help of genetic engineering. For this purpose a vector produced by genetic engineering techniques is used, with the aid of which animal cells are transformed. Into the vector composition a gene is introduced, which encodes a sequence of peroxiredoxin isolated from helninths (Chandrashekar R. et al., U.S. Pat. No. 6,352, 836, 2002). Simultaneously with using the vector, the authors propose additionally to use protein as a means for stimulating the immune system of animals. It should be noted that the use of gene therapy for treating mammals has not received rapid development because of its being costly and a large number of side effects having been revealed.

Experiments are known on direct use of naturally occurring peroxiredoxins Prx VI in treating chemical burns of the respiratory organs in rats (Novoselov V. I. et al., 2000). A disadvantage of such method was the expensiveness of obtaining natural peroxiredoxin in preparative amounts.

A method for treating AIDS (HIV-1) is known (Lynn R. G., Walker B. D., PCT Appl. WO02077294, 2002), according to which a recombinant peroxiredoxin is used as a drug component. As the main method of treating it is proposed to employ a system for purifying biological samples, such as blood, plasma, serum, saliva, etc. In the purifying system a contact is formed between the cells subjected to infection and entering into the composition of the sample and peroxiredoxin whose concentration is at least 5 μg/ml for a period of time required for inhibiting the action of virus particles and restoring the functions of the organism.

In terms of the homology of amino acid sequences and immunological affinity, all the so far known peroxiredoxins of mammals can be classed into the following groups: Prx I-Prx IV, Prx V and Prx VI. The homology of proteins belonging to the same groups is more than 90%. Peroxiredoxins Prx I-Prx V belong to the group of 2-Cys thiol-specific antioxidants. The group Prx V and Prx VI, the inconsiderable in number, represented by1-Cys peroxiredoxins, strongly differs from other groups and has only 20-40% of amino acid sequences common with the peroxiredoxins of other groups.

The family of peroxiredoxins is noted for high conservatism, and its representatives have been detected in the genomes of practically all live organisms, from bacteria to man. According to the data of immuno-histochemical investigations, obtained with the help of light microscopy and in situ hybridization, peroxiredoxin Prx VI is detected practically in all animal tissues. However, its maximum concentration has been revealed predominantly in tissues directly contacting the atmosphere, namely: in the olfactory epithelium, trachea, pulmonary bronchi, skin epidermis, and hair follicles (Novoselov S. V. et al., 1999). Immuno-histochemical investigations with the help of electron microscopy have shown that Prx VI is the sole secretory peroxiredoxin identified today. It is synthesized in specialized cells (goblet cells of the respiratory epithelium and supporting cells of the olfactory epithelium). By direct biochemical and immunological investigations on rats it was shown that in the trachea, pulmonary bronchi and olfactory epithelium the Prx VI contribution to the neutralization of active forms of oxygen is 70-80%. Similar results were obtained for the human trachea and bronchi. For instance, in the composition of the mucus of epithelium trachea the Prx VI concentration is at least 15 μg in 1 mg of protein.

Methods of obtaining natural peroxiredoxin are known (Pesenko I. V. et al., 1998, Novoselov S. V. et al., 1999). These methods comprise isolating tissue from the organs of mammals, its accumulation and homogenization, extraction of target protein, and also fine fractionation of the preparation with the aid of three consecutive chromatographic stages. The main disadvantages of obtaining Prx VI from natural sources are: the necessity of accumulating animal tissues, small ultimate yield of pure preparation (0.01 mg per animal), and the possibility of the origination of allergic reactions when using foreign protein for the treatment of man.

A recombinant protein Prx VI can be obtained by using various expression systems (Sang W. K. et al., 1998; Chen J. W. et al., 2000; Pesenko I. V. et al., 2001).

It is known to obtain recombinant protein Prx VI in prokaryotic cells of the E.coli strain BL21 (Chen J. W et al., 2000). For this purpose a fragment of Prx VIhum HA0683 cDNA (GENBANK™ D14662) was taken, having a length of 1653 b.p., containing an open reading frame for Prx VIhum. The major part of the starting fragment (having a length of 1044 p.b.) was inserted into the expression vector pET28c along the HindIII restriction site. The obtained construct provided producing recombinant protein which, along with Prx VIhum amino acid sequence, contained 42 additional amino acid residues, including six His residues at the N-terminal of the protein polypeptide chain. Having taken the same Prx VIhum fragment as a basis and artificially introduced sites for the recognition of NdeI and XhoI restrictases, the authors amplified the encoding region. The obtained fragment was cloned along these sites into the expression vector pET21b. As a result, the recombinant protein whose biosynthesis was determined by this plasmid contained two additional amino acid residues, apart from six His residues on the polypeptide chain of the product. After the transformation of E. coli by the obtained DNA and the induction of the gene expression by isopropylthiogalactoside (IPTG), the cells were grown for 6 hrs and destroyed. Protein preparations were subjected to sequential purification by chromatographic techniques. Though introducing additional His residues into the polypeptide chain composition appreciably simplifies isolation of recombinant proteins, modifications of such kind noticeably shift the isoelectric point of protein products compared with natural proteins and, as a consequence, change their electrostatic microenvironment.

Expression of recombinant Prx VI in eukaryotic cells is known (Fujii T. et al., 2001). For this purpose from various rat tissues a mixture of mRNA was isolated, using which a complementary DNA chain was synthesized by a inverse polymerase reaction. Then this cDNA was subcloned into baculovirus shuttle vector pVL1392. The obtained construct provided producing a full-sized rat Prx VI in infecting eukaryotic cells Sf21. This method is not free of such disadvantages as long time required for producing the preparation, necessity of using expensive nutrient media, a low yield of the target product, compared with bacterial systems, and the possibility of origination of allergic side reactions when using rat Prx VI in medicinal compositions.

It is known that it was proposed to use as a drug component fragments of peroxiredoxin or its modifications, including proteins with replacements and deletions in the amino acid sequence for treating AIDS (Lynn R. G., Walker B. D., PCT Appl. WO02077294, 2002). These proposals are not supported by examples of the functional activity of selected protein fragments for the treatment of other types of diseases except virus diseases. Besides, the selected fragments relate to using conservative portions of the sequence of 2-cys peroxiredoxins, located in the regions of the N and C terminals of the sequence, this being not a matter at issue of the present invention.

ESSENCE OF THE INVENTION

The present invention relates to a pharmaceutical composition for the antioxidant protection of cells, tissues and an organism as a whole against hyperproduction of free radicals, in the formulation of which as the main active compound there enters an effective amount of at least one antioxidant selected from the group consisting of i) a peroxiredoxin, ii) a peroxiredoxin fragment, iii) a dihydrolipoic acid, iv) a combination of i) and ii), i) and iii), ii) and iii), i) and ii) and iii) and pharmaceutically acceptable additives. The pharmaceutical composition can comprise peroxiredoxins selected from the group consisting of PrxI, PrxII, PrxIII, PrxIV, PrxV and PrxVI, separately or in combination with a therapeutic agent. The therapeutic agent is selected from the group of i) antibacterial, antivirus, antifungal, antihistaminic preparations, ii) high-molecular enzymes which provide additional protection against free radicals, iii) low-molecular compounds which provide additional lowering of the level of free radicals inside the cell, iv) preparations employed for the transplantation or cryopreservation of organs, v) biologically active proteins, vi) hormones, vii) vitamins.

Another subject of the invention is a method for enhancing the antioxidant protection of the cells, tissues and organism of mammals, according to which a contact is provided of an effective amount of peroxiredoxin and/or of its fragment entering into a pharmaceutical composition with the intracellular space. The contact with the intracellular space of a tissue, organ or organism as a whole is effected either by means of passive or active diffusion through the agency of applications, drops, spraying, sublingual, vaginal or rectal administration, or by delivery with the aid of parenteral or endolumbal introducing by injections. The antioxidant protection from exogenous and/or endogenous pathology-inducing factors is carried out preliminarily to and/or in the process of development of a pathology and/or during the rehabilitation period.

A further subject of the invention is a method of producing natural human protein of peroxiredoxin Prx V1hum or of the N-terminal fragment of peroxiredoxin ΔPrx V1hum which has a similar antioxidant effectiveness but a smaller size and a higher permeability in the intercellular space. In accordance with this method, selection a fragment of a nucleic acid molecule for protein encoding is carried out, an expression vector for the transformation of cells is produced, the transformation of cells is carried out, the cultivation of cells is performed under conditions providing the production of said protein and/or a fragment thereof, and subsequent isolation of protein from the cell culture is carried out.

To yet another subject of the invention there relates a nucleic acid molecule encoding a protein having antioxidant properties. The nucleic acid molecule is a DNA or RNA and includes a nucleotide sequence corresponding to the amino acid sequence of natural human protein of Prx V1hum (SEQ ID NO: 1) having a length of 224 a.b. or an N-terminal DNA fragment of peroxiredoxin ΔPrx V1hum (SEQ ID NO: 2) having a length of 177 a.b. or an N-terminal DNA fragment of peroxiredoxin ΔPrx V1hum, whose length is selected within the range of from 178 a.b. to 223 a.b. inclusive.

A still further subject of the invention is a recombinant plasmid for producing natural human protein of peroxiredoxin Prx V1hum or a fragment of peroxiredoxin ΔPrxV1hum, which plasmid under control of a phage T7 promoter an open reading frame which comprises a start ATG codon, a human peroxiredoxin cDNA or a peroxiredoxin fragment cDNA and a stop codon which provide its expression in a compatible host cell.

To yet another subject of the invention there relates a strain or cell line which are produced by the transformation of cells by a vector which is a producer of natural human protein of peroxiredoxin Prx V1hum or of a fragment of peroxiredoxin ΔPrx V1hum. The cells are selected from the group consisting of prokaryotes or eukaryotes.

LIST OF FIGURES

The present invention is illustrated by FIGS. 1-11.

FIG. 1 is a physical map of plasmid pET23-a-Prx V1hum. In the upper part the disposition of the cDNA of peroxiredoxin Prx V1hum and of unique restriction sites in the polylinker is shown.

Figure 2:
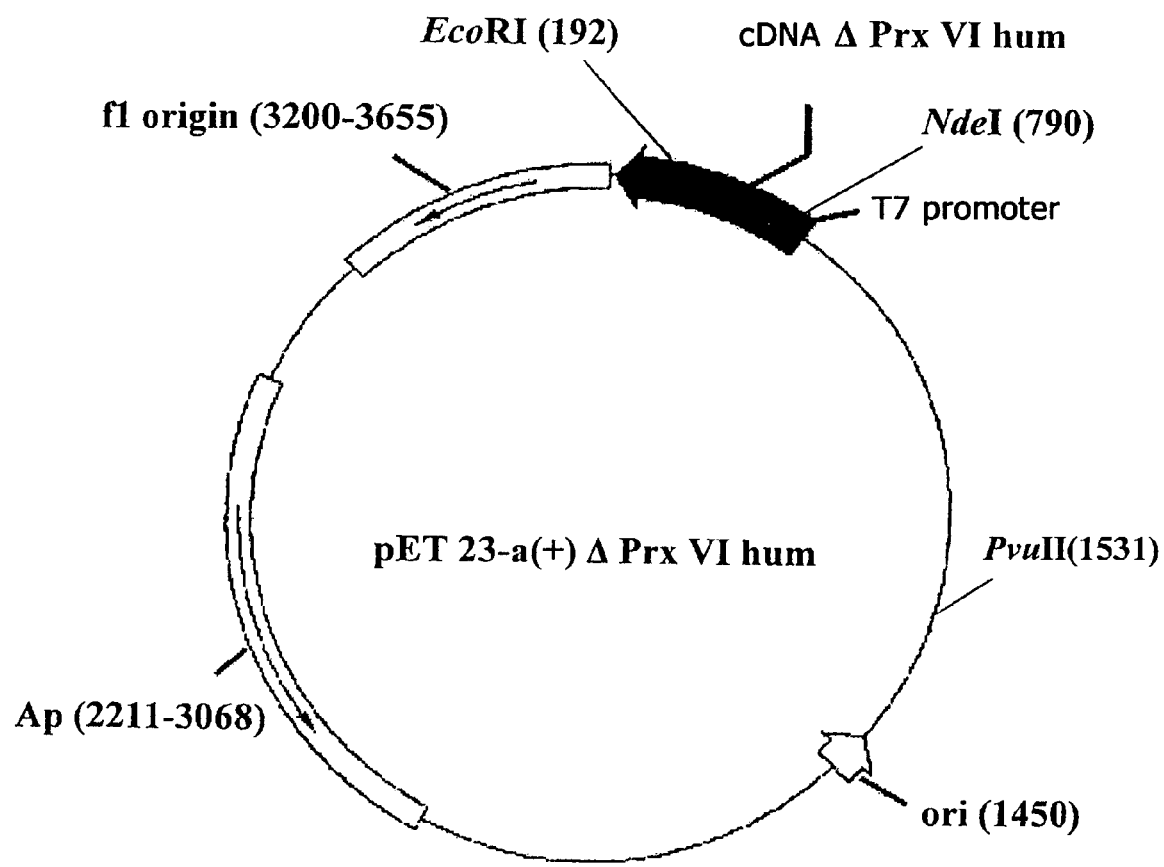

FIG. 2 is a physicals map of plasmid pET23-a(+)ΔPrx V1hum. Endonuclease restriction sites are indicated. Ori is an origin of plasmid replication. AP is a genetic marker which determines the resistance of E. coli cells transformed by plasmid pET23-a(+)ΔPrx V1hum to ampicillin.

Figure 3:
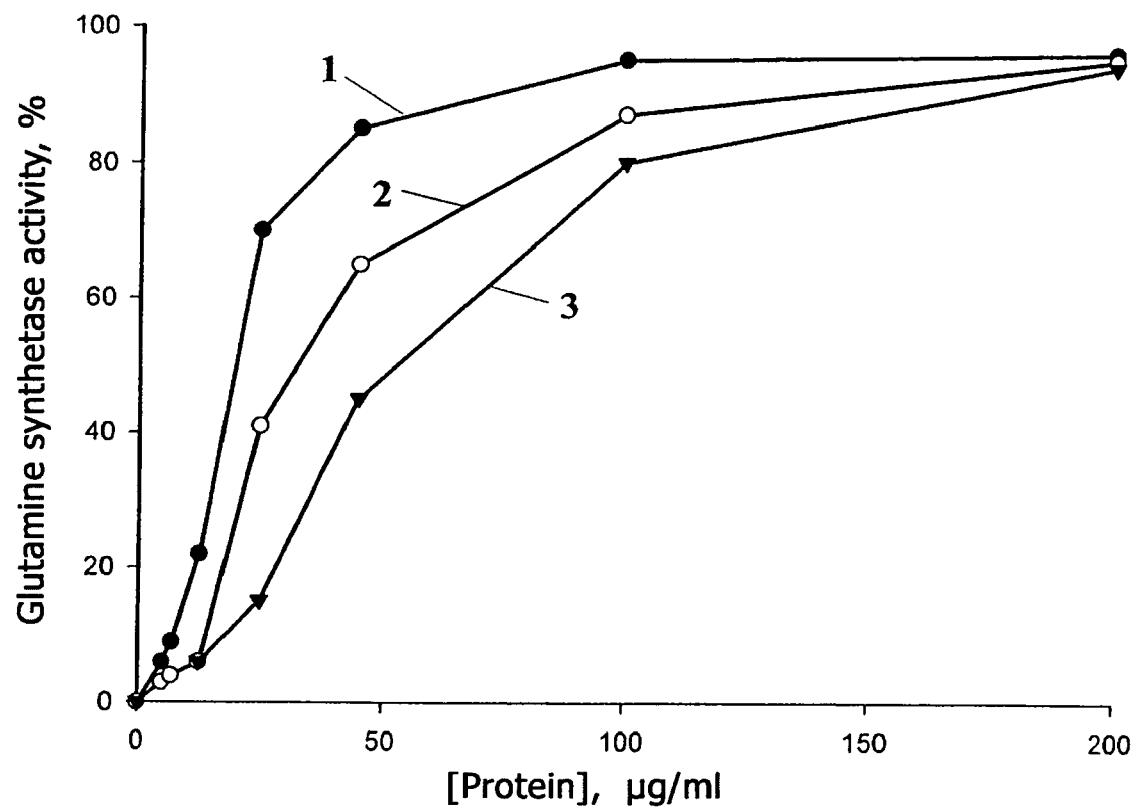

FIG. 3 presents an intercomparison of the protector properties of natural rat Prx V1rat (shown at 1), recombinant Prx V1hum (shown at 2) and its N-terminal fragment ΔPrx V1hum (shown at 3) in terms of protecting E.coli glutamine synthetase from inactivation in a model oxidative system in vitro.

Figure 4:
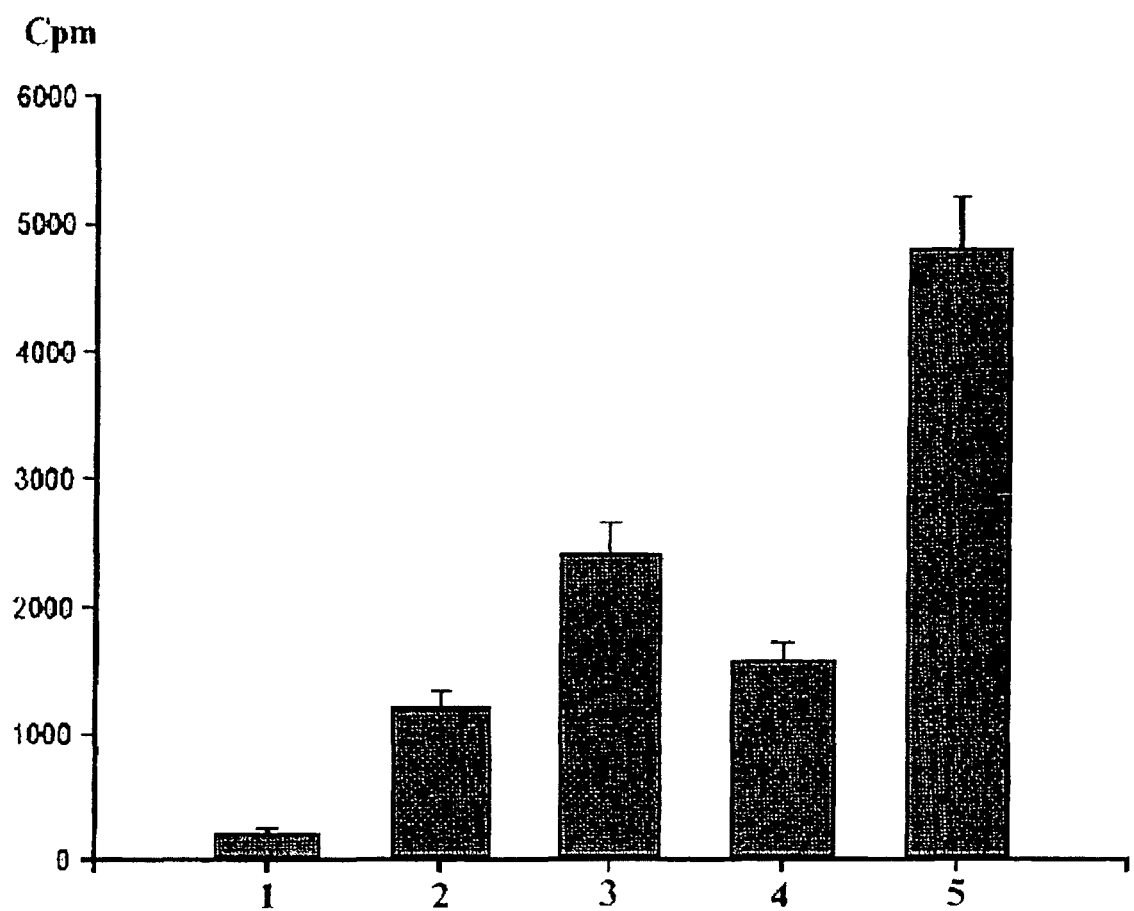

FIG. 4 shows the incorporation of $^3$H-thymidin into concanavalin A-stimulated murine lymphocytes in the presence of Prx V1hum. Wherein: 1 is the medium, 2 are T-cells without concanavalin A stimulation, 3 are concanavalin A-stimulated T-cells, 4 are T-cells in the presence of Prtx V1hum, 5 are T-cells stimulated with concanavalin A in the presence of Prx V1hum.

Figure 5:
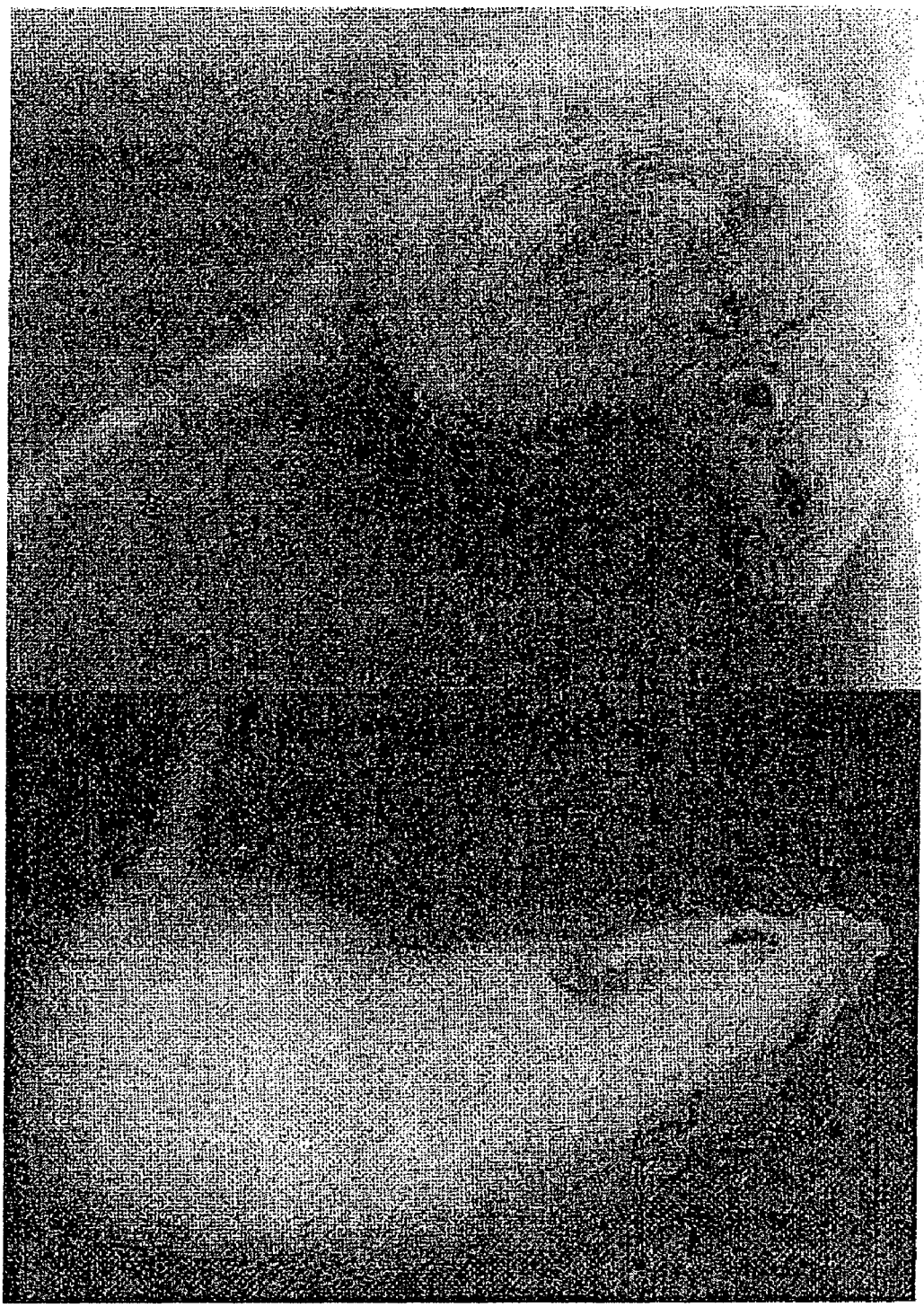

FIG. 5 shows an external appearance of rats 12 months after gamma irradiation (600 roentgen units). Wherein: A is control; B is a rat with recombinant Prx V1hum administered before the irradiation.

Figure 6:
Figure 6:
Figure 6:

FIG. 6 shows tracheal epithelium of a rat after burn with acid vapors and subsequent application of natural rat or recombinant Prx V1hum. Application was carried out 1 hour after the burn. Wherein: A is control; B is epithelium 24 hours after chemical burn; C is epithelium 24 hours after chemical burn with Prx V1hum applied one hour after the burn; E is tracheal epithelium, BM is basal membrane. Almost complete preservation of all epithelial cells is observed.

Figure 7:
Figure 7:
Figure 7:

FIG. 7 shows restored cell epithelium of a rat trachea 14 days after burn with vapors of hydrochloric acid. Wherein: A is control, B is epithelium 14 days after chemical burn, C is epithelium 14 days after chemical burn with Prx V1hum application, E is tracheal epithelium, BM is basal membrane, F are phagocytes. Therapy was carried out 24 hours after burn, during 5 days. Solution of a pharmaceutical composition based on recombinant Prx V1hum was applied once a day.

Figure 8:
Figure 8:
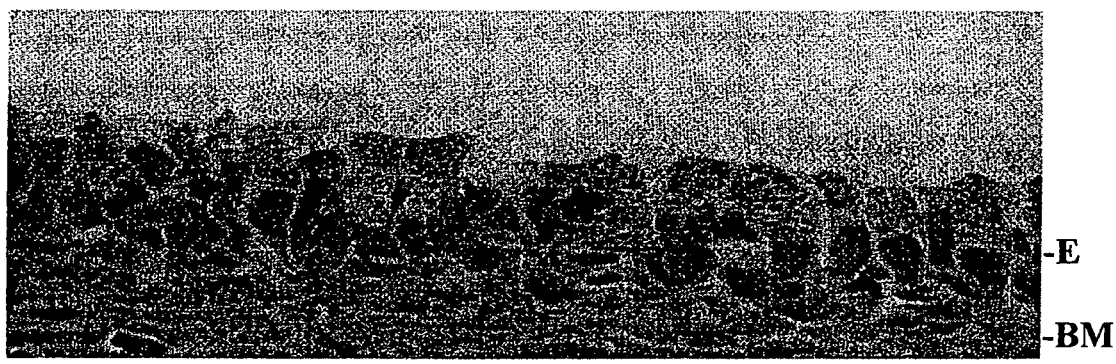
Figure 8:
Figure 9:
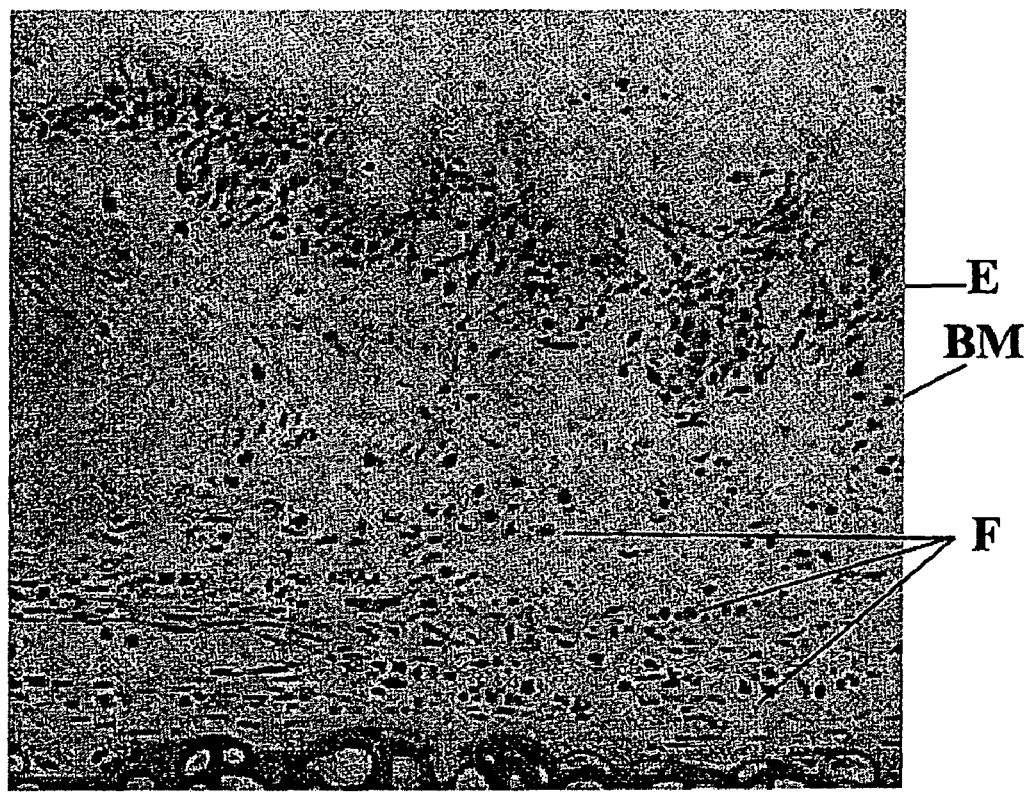
Figure 9:

FIG. 8 shows tracheal epithelium of a rat after application of a lipopolysaccharide. Wherein: A is norm, B is one hour after application, C is 3 hours after application, E is tracheal epithelium, BM is basal membrane, F are phagocytes. Significant death of epithelium cells and appearance of a large number of phagocytic cells are observed;

FIG. 9 shows tracheal epithelium of a rat after application of a lipopolysaccharide and subsequent application of recombinant Prx V1hum. Wherein: A is control without use of Prx V1hum, B is the result of using Prx V1hum after application of liposaccharide, E is tracheal epithelium, BM is basal membrane, F are phagocytes. Prx V1hum was applied immediately after the application of lipopolysaccharide.

Figure 10:
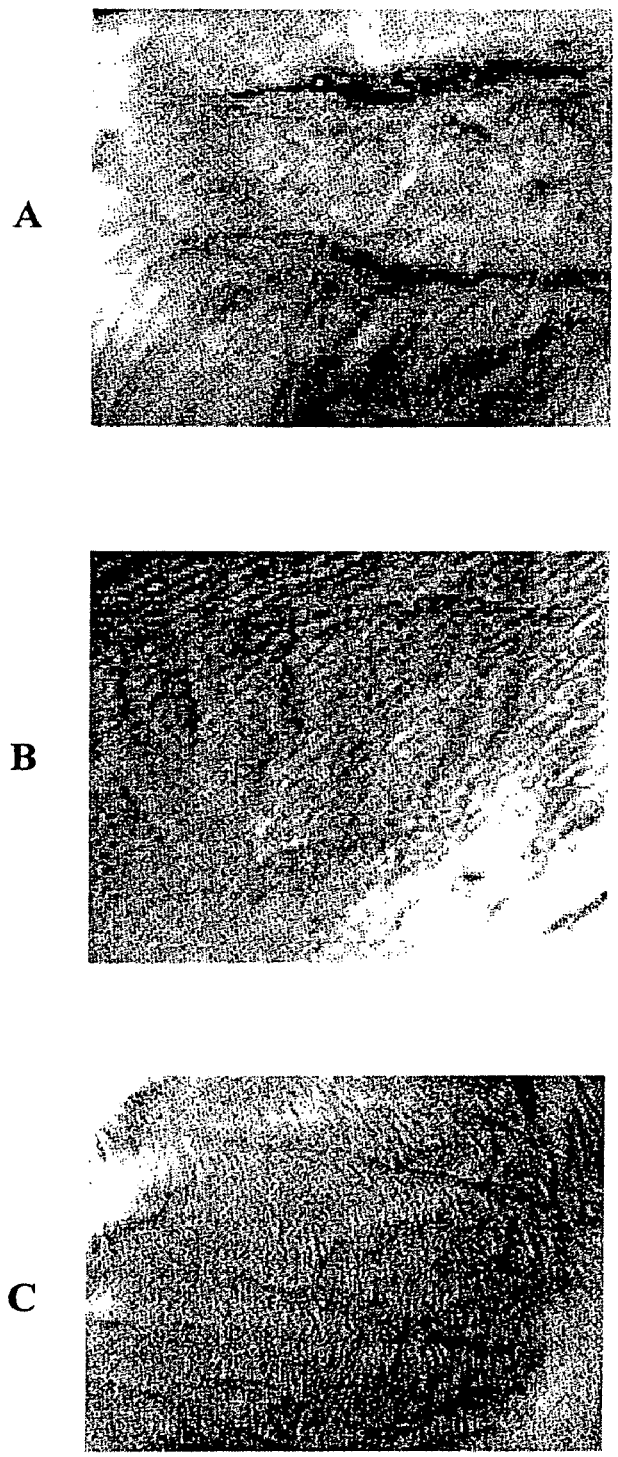

FIG. 10 shows using peroxiredoxin Prx V1hum or its fragment ΔPrx V1hum for treating wounds. Wherein: A a bactericidal plaster was used for treatment, B application of Prx V1hum to wound was carried out, C application of Prx ΔV1hum to wound was carried out.

Figure 11:
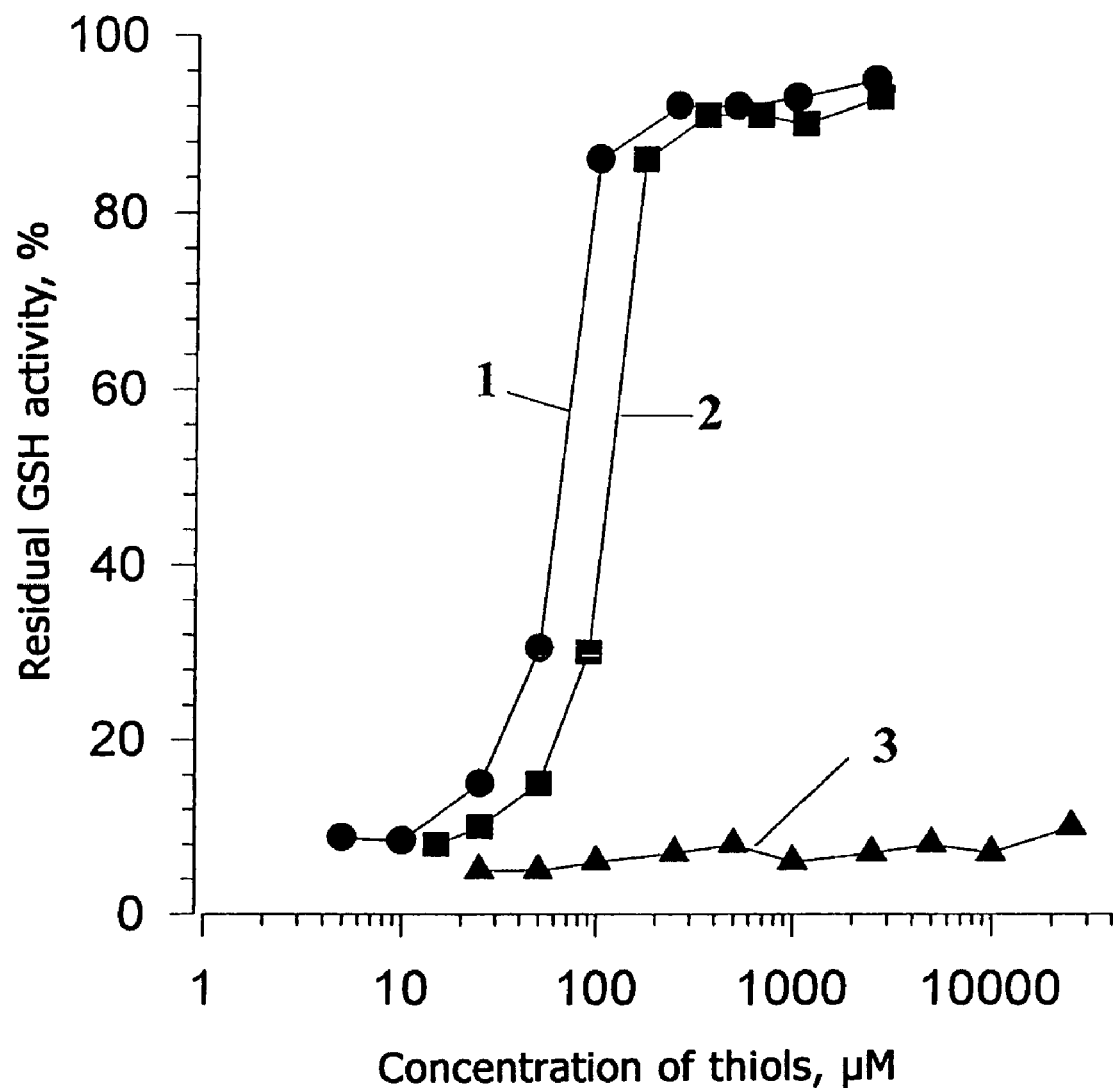

FIG. 11 shows comparative characteristics of the antioxidant properties of 1-dithiotreitol, 2 -lipoic acid and 3 -dihydrolipoic acid. The antioxidant activity was determined from the degree of glutamine synthetase protection against metal-catalyzed oxidative system. The antioxidant effectiveness of thiols was determined in molar concentration, at which 50% protection of glutamine synthetase took place.

DESCRIPTION OF THE INVENTION

The present invention relates to methods of treating or preventing diseases caused by an imbalance between oxidation and reduction processes in the cells and organisms of mammals with the aid of pharmaceutical compositions in the formulation of which as the main active component there enters at least one antioxidant selected from the group consisting of: i) a peroxiredoxin, ii) a peroxiredoxin fragment, iii) a dihydrolipoic acid, iv) a combination of: i) and ii), i) and iii), ii) and iii), i) and ii) and iii). The pharmaceutical composition can comprise peroxiredoxins selected from the group consisting of: PrxI, PrfxII, PrtxIII, PrxIV, PrxV and PrxVI.

As an example which supports but does not limit the essence of the present invention, a method of preparing human peroxiredoxin Prx VIhum whose gene is isolated from myeloblast cells is cited (Nagase T. et al., 1995, EMB/GenBank D1 4662, HA0693). The size of the peroxiredoxin fragment of Prx VIhum DNA (SEQ ID NO: 1) is 672 b.p. The length of the nucleic acid encoding the polypeptide is 224 amino acid bases. In Example 2 a variant of constructing a recombinant plasmid pET23-a-Prx VIhum DNA which encodes a full-size peroxiredoxin Prx VIhum is considered.

Another example which supports but does not limit the present invention relates to a method for producing at least one type of fragment of human peroxiredoxin ΔPrx V1hum, which relates to the N-terminal of nucleic acid fragment, whose length is selected within the range of from 177 to 224 a.b. In Example 3 a variant of constructing a recombinant plasmid DNA pET23-a(+)ΔPrx V1hum is considered, which encodes the N-terminal fragment of human peroxiredoxin ΔPrx V1hum (SEQ ID NO: 2) having a length of 177 a.b. with a molecular mass of 19691.61 Da, contains EcoRI-NdeII—a fragment of plasmid pET23-a(+) comprising RNA polymerase phage promoter T7, an origin of replication (ori), a genetic marker (Ap), unique which determines the resistance of E. coli cells transformed by plasmid pET23-a(+)ΔPrx V1hum to ampicillin, unique sites of recognition by restriction nucleases with the following coordinates: NdeI-790, EcoRI-192, PvuII-1531 and NdeI-EcoRI fragment having a length of 552 b.p. with the sequence ΔPrx V1Hum. The recombinant plasmid DNA pET23-a(+) ΔPrx V1hum has a size of 4210 b.p. The advantages of the proposed construct are attained due to the fact that the ΔPrxV1hum fragment which enters into this construct encodes a polypeptide shortened as compared with Prx VIhum, which preserves the antioxidant activity of natural protein. This, in the first place, simplifies chromatographic purification of ΔPrxV1hum; in the second place, it makes more adaptable the use of ΔPrxV1hum in the formulation of medicinal compositions owing to better penetrability into tissues; in the third place, it increases the proportion of the target product in the overall biomass of the producing strain, this, in its turn, leading to a reduction of the cost price of the final product.

Within the framework of the present invention, in Example 4 there is considered a method for producing a functionally active full-sized recombinant peroxiredoxin ΔPrxVIhum or of its N-terminal fragment ΔPrxV1hum, which comprises cultivation of a strain or a line of cells transformed by a plasmid under conditions which provide producing said protein or its fragment and subsequent isolation of recombinant protein from the cell culture. The cells entering into the strain or into the line of cells are selected from the group consisting of prokaryotes, e.g., from a bacterial culture of E.coli, or of eukaryotes, such as yeast cells, plant cells, animal cells or insect cells.

The recombinant PrxVIhum synthesized according to the method of the invention has antioxidant characteristics close to the characteristics of PrxVIrat isolated from the olfactory epithelium of rat.

Neither natural PrxVIrat nor recombinant PrxVIhum peroxiredoxins produced any effect on the number of live cells of the line L929, and the level of the proliferation of T-lymphocytes stimulated with concanavalin A increased approximately twofold as against the level of the proliferation of cells stimulated only with concanavalin A (see Example 7). Therefore a conclusion can be drawn that the tested compounds are low-toxic.

Peroxiredoxin is shown to distribute effectively in various tissues of an organism after intravenous administration of a composition into whose formulation recombinant PrxVIhum labeled with fluorescein isothiocyanate is included (see Example 9). 15 minutes after a composition with peroxiredoxin PrxVIhum was injected into the vein of a rat, said compound distributes uniformly among all the organs of the rat, including the brain. Thus, the method of intravenous administration of recombinant PrxVIhum makes it possible to increase its content almost in all tissues of the organism.

The multifunctional applicability of peroxiredoxin as an effective antioxidant is supported by examples of treating diseases in mammals, caused by both exogenous and endogenous factors entering into the group: a) ionizing radiation, b) chemical burn, c) acute inflammatory process, d) wounds. The given examples include but do not limit other applications of peroxiredoxin for the prevention and/or treatment.

Peroxiredoxin the PrxVIhum type comes into but does not limit the range of peroxiredoxins which have high antioxidant activity and can be used for making medicaments.

Radioprotector Properties of Peroxiredoxins

The antiradiation properties of Prx VIhum are investigated both in vitro, by investigating a solution of hemoglobin, and in vivo on animals. Irradiation of a solution of hemoglobin (see Example 10) leads to essential changes in its structure (appearance of peaks at 635 nm and an increase of light scattering), this being indicative of conversion of oxyhemoglobin to methemoglobin, followed by the aggregation thereof. Adding Prx VIhum to the solution of hemoglobin in a concentration of about 50 μg/ml before the irradiation leads to considerable lowering of the formation of oxidized forms of hemoglobin, the concentration of which lowered almost to zero.

The radioprotector properties of peroxiredoxin in experiments in vivo are determined on an example of protecting animals from the action of gamma-irradiation in a sublethal dose with an intensity of 6 Gy. The data supporting the radioprotector properties of peroxiredoxin Prx VI are presented in Table 1 and in Example 13. Direct single injection of recombinant PrxVIhum into a vein 30 minutes before the irradiation made it possible to increase sharply the number of survived animals as against control and to diminish the number of irradiation-associated malignant neoplasms.

TABLE 1

Survival of rats administered with Prs VIhum before irradiation. Groups of 6 rats were simultaneously subjected to gamma-irradiation at a dose of 6 Gy. The number of rats survived in each group during the indicated period of time is listed in the Table.

|  | 3 months | 6 months | 12 months | 15 months |
| --- | --- | --- | --- | --- |
| Control | 4 | 3 | 2 | 1 |
| Prx VIhum | 6 | 5 | 4 | 4 |

Peroxiredoxin as a radioprotector can be used as a component of pharmaceutical compositions for the prevention or treatment of a wide range of diseases. These diseases may be caused by: a) ionizing radiation (first of all, in radiotherapy, in preventive investigations, in cases of the personnel operating with radiation sources), b) space radiation which affects first of all, cosmonauts and pilots, c) radionuclide contamination caused by intaking food, water or air contaminated with radionuclide, d) action of non-ionizing radiation, e.g., in tomographic examination, e) action of ultraviolet radiation sources on the organism (sunlight, welding, pulsed sources of light, displays). For preventing or lowering the effect of hyperproduction of free radicals, it is possible to use antidotes with peroxiredoxins introduced into them. The formulation of the antidotes should be oriented to that type of exogenous action existing in the zone where equipment repair operations, emergency remedial operations or post-disaster remedial operations have to be carried out.

Treating Inflammatory Processes Caused by Exogenous Factors

Chemical burn was selected to exemplify an exogenous factor. The action of a chemical burn was simulated in accordance with Example 14. For developing a more effective method of treatment, the pathology progression stages after the effect of burn were investigated.

In the first stage we investigated the dynamics of variations in the level of neutrophils and antioxidant enzymes in the cell epithelium of rat trachea after burn with vapors of hydrochloric acid. Two periods of sharp increase in the number of active neutrophils were observed: 40 minutes and 6 hours after the burn. A sharp increase in the number of active neutrophils deepens the extent of injury, because neutrophils release hydrogen peroxide.

Biochemical investigations (see Example 9) showed that the level of peroxiredoxin Prx VIrat activity in the epithelial cells increases approximately twofold immediately after burn. At the same time, the activity of superoxide dismutase, catalase and glutathione peroxidase, which are the main antioxidant enzymes in the organism, lowers in the tracheal mucus by approximately 30%. In 24 hours the activity level of all the above-cited enzymes, including peroxiredoxin Prx VIrat, was lowered.

Histochemical investigations showed that, 40 minutes after the burn, processes of death of ciliary epithelium cells commence in the tracheal epithelium and bronchi, which later on become avalanche-like. Maximum death of the epithelial cells of the upper respiratory tract mucosa is observed 24 hours after the burn. There takes place almost complete death of the cells of ciliated epithelium which is responsible for mucociliary transport in the trachea and bronchi. This condition of the epithelium was adopted as control for comparative evaluation of the extent of burn and of the effectiveness of treatment.

The inflammatory process caused by a chemical burn is characterized by two pathology progression periods after the chemical burn: first (to 24 hours after the burn)—a period of the epithelium injury development, and second (after the first 24 hours following the burn)—a period of very slow epithelium restoration. Without treatment, a partial restoration of the epithelium of tracheal mucosa after chemical burn is observed in 30 days.

As one of variants of treating mammals after a chemical burn of the upper respiratory tract, which includes but does not limit other methods of delivering a medicament to the place of injury, we used the variant of applying the rat's upper respiratory tract with a solution whose formulation includes peroxiredoxin Prx VIhum. FIG. 7 shows a section of rat tracheal epithelium 14 days after burn with Prx VIhum applied 5 times every day. An almost completely safe epithelium of the tracheal mucosa is observed, this being indicative of an almost complete regeneration of the ciliary cells of the epithelium. The presence of the elements of mucin in which phagocytes are identified is indicative of the presence of residual inflammatory process in the trachea.

Treating Inflammatory Processes Caused by Endogenous Factors

As another model of an inflammation, we investigated an inflammatory process in respiratory epithelium, caused by toxins of bacterial nature—by lipopolysaccharides (LPS) which are a component part of the external wall of the membrane in most of gram-negative bacteria (see Example 15).

After the application of lipopolysaccharide that causes an acute inflammatory reaction in the trachea of a mammal, we investigated the dynamics of variations in the level of neutrophils, TNF-α and peroxiredoxin Prx VIrat in the cell epithelium of rats' trachea. For determining the characteristics of the method of treating, we carried out investigations of the dynamics of the level of neutrophils and antioxidants, as well as biochemical and histochemical investigations of the effect produced by inflammatory process on the organism of a mammal.

A sharp increase in the number of active neutrophils was observed one hour after the administration of LPS. A sharp increase in the number of active neutrophils, in its turn, deepens the extent of injury, because neutrophils release $H_2O_2$.

Biochemical investigations showed that the level of the activity of peroxiredoxin Prx VIrat in epithelial cells increases approximately twofold an hour after the application of lipopolysaccharide From the data of histological investigations it is seen that in the case of using an LPS concentration equal to $10^{-7}$ mg/animal there is observed massive accumulation of neutrophils in the wall of the trachea, development of edema, followed by exfoliation of mucosa into the lumen of the trachea and death of cells 3 hours later (see Example 15, FIG. 8).

Immuno-histological investigations showed that in many areas of tracheal epithelium already in an hour there was observed mass death of the peroxiredoxin Prx VIrat secreting cells. This led to the absence of Prx VIrat in the mucus covering these areas of the trachea. This condition of the epithelium was adopted as control for comparative evaluation of the extent of the inflammatory reaction and of the effectiveness of treatment.

A direct single application of recombinant Prx VIhum into the trachea of a rat immediately after the application of liposaccharide led to almost complete restoration of the epithelial tissue after 2 weeks (see FIG. 9), whereas in the control group animals given no treatment after the LPS application the ciliary epithelium practically was not restored.

Introducing Prx VIhum into the area of lesion of the epithelial cells prevents the development of secondary alternative disorders, thereby limiting the scope of pathological changes. Neutralization of active forms of oxygen restores proliferative cell processes, contributes to rapid regeneration of damaged epithelium, lowers the risk of development of infectious complications in the lesion focus.

Using other antioxidants, e.g., glutathione, gave no significant effect (see Table 2).

TABLE 2

Integrity of tracheal epithelium upon application of different antioxidants after lesion of tracheal epithelium (according to histological data)

| Time after the action of LPS | | Glutathione | POrx VIhum |
|---|---|---|---|
| 1 hour | 30% | 30% | 90% |
| 3 hours | 20% | 20% | 80% |
| 6 hours | 10% | 10% | 65% |

TABLE 2-continued

Integrity of tracheal epithelium upon application of different antioxidants after lesion of tracheal epithelium (according to histological data)

| Time after the action of LPS | | Glutathione | POrx VIhum |
|---|---|---|---|
| Treatment 24 hours later for 5 days and the integrity of epithelium 2 weeks later | 20% | 20% | 80% |

Treating Wounds

In treating wounds (see Example 16), it is possible to use different methods for administering a composition containing 0.5 μg/ml of peroxiredoxin Prx VIhum and/or 1,5 μg/ml of its fragment ΔPrx V1hum into the intracellular space of the lesion area. Nevertheless, even conventional application of the composition in a thin layer and/or application to the place of lesion and passive diffusion of Prx V1hum and/or ΔPrx V1hum molecules into the intracellular space leads to a more rapid and complete healing of the wound. A feature peculiar to wounds to which peroxiredoxins were applied was that the process of wound healing did not enter into a long inflammatory phase which is caused, according to the literature data, by an infection. Application of peroxiredoxin contributed to speeding up englobung of the infection by neutrophils and macrophages in the wound and was thereby the cause of speeding up headlining of wounds. Our histological investigations showed that upon application of both peroxiredoxins to a wound the cicatrix was appreciably smaller than upon application of a bactericidal plaster. A comparison of the cell composition of the cicatrix 8 days after the surgical incision showed that the application of both peroxiredoxins decreased essentially the number of neutrophils, macrophages, thrombocytes, lymphocytes and erythrocytes that are typical of the inflammatory phase of wound regeneration. Besides, the number of young fibroblasts in a cicatrix upon application of peroxiredoxins was substantially smaller. The effect of the application of a peroxiredoxin or its fragment to a wound as against the treatment of a wound with a bacterial plaster is shown in FIG. 10.

A Method for Preventing or Treating a Disease Caused by Hyperproduction of Free Radicals In the course of experiments on simulating exogenous and endogenous effects on the organism of animals a fact was discovered that introducing into the fluid medium of an organism (including blood and lymph) and/or into the intercellular space of tissues, organs or of an organism as a whole a pharmaceutical composition into whose formulation there enters at least one type of a peroxiredoxin, leads to a high effectiveness of the prophylaxis and/or treatment of a large group of diseases accompanied by the hyperproduction of free radicals.

In the general case, the method for treating diseases in which it is useful to compensate for the hyperproduction of free radicals in tissues organs or in an entire organism of mammals consists in introducing into the intercellular space of cells, tissues or of an organism as a whole a composition into the formulation of which as the main acting component there enters an effective amount of at least one antioxidant selected from the group consisting of: a) a peroxiredoxin, ii) a peroxiredoxin fragment, iii) dihydrolipoic acid, iv) a combination of i) and ii), i) and iii), ii) and iii), i) and ii) and iii) and pharmaceutically acceptable additives. The pharmaceutical composition can comprise peroxiredoxins selected from the group consisting of: PrxI, PrxII, PrxIII, PrxIV, PrxV and PrxVI, separately or in combination with a therapeutic agent. Introducing the composition into the intercellular space of tissues, organs or into the organism of a mammal as a whole is effected by application, injection or other methods known in the medical practice of employing biologically active peptides.

The proposed method relates to different variants of the prophylaxis or treatment of tissues, organs or the organism of mammals as a whole, comprising:

A) preventive protection of an organism, individual organs or individual areas of normal tissue against the hyperproduction of free radicals, caused by: i) ionizing radiation, e.g., in the course of treating cancer or in flights at high altitudes and in space flights, ii) the effect of thermal and/or chemical burns during disaster relief and fire suppression operations, iii) a combination of i) and ii) factors.

B) protection of organs intended for transplantation or for improving the possibility of cryopreservation.

C) protection of organs against inflammatory processes caused by mechanical injuries of the skin and tissues as a result of traumas, injections of medicaments or surgical operations.

The duration of the application and dosage characteristics of the medicaments containing peroxiredoxins are determined depending on the kind of therapy or prophylaxis. In the course of symptomatic therapy caused by cough or itch, it is sufficient to administer single doses. Pathogenetic therapy directed to the suppression of disease mechanisms requires administering preparations which suppress the hyperproduction of radicals in the course of disease treatment. When the oxidation-reduction balance in the organism of a mammal is disturbed because of ailment of a particular organ, a substitutive therapy is required, and the treatment requires doses of the antioxidants (peroxiredoxins) sufficient for compensating and restoring the functions of the organ. In the course of etiotropic therapy the administration of peroxiredoxin-containing medicines, e.g., via a dropper, is carried out during the period of eliminating poisons or other exogenous substances from the organism. It is most preferable to use compositions and medicines containing peroxiredoxin for carrying out complex therapies. In recent years, in connection with a wide spread of cardiovascular diseases, disorders of the immune system, treatment of AIDS, alcohol and drug addiction, peroxiredoxin-based preparations can be used in supporting therapy along with other long-term administration preparations.

Proceeding from the results of examining the condition of the tissue, organ or organism as a whole, the treatment procedure is determined, selected from the group consisting of: a) single or repeated application or spraying of a solution of a pharmaceutical composition or drug onto the injured area, b) single or repeated injections of a solution of a pharmaceutical composition or drug, c) single or repeated taking of tabletted, powder or liquid dosages sublingually or in the form of dusts, pastes, suppositories, ointments, gels for applying to the skin and epithelium surface, or by combining said procedures.

Transfer of the active peroxiredoxin component into the intercellular space of the tissue, organ or organism as a whole is effected either with the aid of passive or active diffusion in applications or spraying or by transferring Prx V1hum or ΔPrx V1hum or a combination thereof with an activator via blood or in combination with blood components (plasma, serum) or in combination with blood substitutes (e.g., with perftoran) or via lymph.

The composition can be introduced into the intercellular space of the tissue, organ or organism in various ways. Since peroxiredoxin, when passing through the gastrointestinal tract, is liable to degradation and loss of biological activity, the main introducing procedure is parenteral administration. In parenteral administration use is made of injections, infusions, inhalations, introduction into a drainage. The solution for injections is introduced intramuscularly, intravenously in shock doses or prolonged infusions, intra-arterially; intrathecally, intraventricularly, endolubally. The solution, powder or tabletted forms can be used sublingually. In some cases vaginal or rectal administration of the preparations is required. It is possible to introduce the composition as drops into the nose or eye, or with the aid of lavage or clysters.

The methods for delivering the composition to the place of inflammation of epithelial tissues, cited in the present specification, do not limit the use of other known methods of delivering biologically active polypeptides to the place of inflammation or injury.

It is preferable, before starting the treatment of inflammatory processes, to investigate the level of neutrophils and/or the concentration of antioxidants in the invaded tissue or organism. For this purpose use is made of a procedure of determining the peroxiredoxin concentration in biological samples with the aid of polyclonal rabbit antibodies against recombinant peroxiredoxin (see Example 11). Basing on the obtained data, the treating procedure selected from the group of a simple or repeated contact of the composition with the zone of inflammation of the tissue or organ and periods of applying the composition are chosen.

The minimum effective amount of the pharmaceutical composition is determined and the treatment is carried out by proceeding from the gravity of the inflammatory process.

For instance, when treating inflammatory processes of the upper respiratory tract, the peroxiredoxin-containing composition is introduced into the nose and/or trachea and/or lung bronchi. For application use is made either of a solution of the composition or the solution is pre-atomized to convert the composition into an air-and-drop mixture, or the composition is used in the form of a dry finely dispersed powder, or the composition is immobilized into finely dispersed granules or nanoparticles of 0.1 to 7000 nm in diameter (see, for instance, Esenaliev, 2000), or the composition is immobilized in liposomes (see, e.g., Thibeault D. W. et al., 1991).

When treating skin injuries, the composition is applied in a thin layer and/or an application is made on the injured place. The methods of delivering the composition to the place of inflammation of epithelial tissues, presented in the specification do not limit the use of other known methods of delivering biologically active polypeptides to the place of inflammation or injury.

When preventing or treating diseases associated with ionizing or non-ionizing radiation, the concentration of at least one type of peroxiredoxin is selected depending on the intensity of the ionizing or non-ionizing radiation effect, taking into account the parameters of a mammal (its weight, age, condition of the organism). In the course of treatment or prevention, the selected formulation of the composition is introduced once or repeatedly before or after the interaction of the organism with ionizing or non-ionizing radiation.

When preventing and/or treating the hyperproduction of free radicals, caused by the simultaneous action of ionizing radiation and/or thermal and/or thermal and/or chemical burn and/or organism contamination with radionuclides owing to intaking food, water or air contaminated therewith, a combined method of peroxiredoxin administration is used, by simultaneous intravenous injections and applications to the injured place, whereby it becomes possible to lower the organism toxication and prevent the uncontrollable death of cells.

In the pharmaceutical composition it is possible to use different types of peroxiredoxins (Prx-PrxIV), since the distribution of the concentrations of different types of peroxiredoxins is different, depending on the type of tissue or organ (Knoops B. et al., 1999). For forming variants of compositions, it is preferable to use a combination of several types of peroxiredoxins which have maximum concentration for each particular organ or tissue. It is possible to use recombinant peroxiredoxins produced from cells of vegetable or animal origin after their selection with the help of tests for biological activity and ability not to induce allergic reactions. For instance, for treating inflammatory processes in epithelial tissues, it is more preferable to use recombinant Prx V1hum and/or ΔPrx V1hum which have stronger antioxidant characteristics compared with types I-V of peroxiredoxins.

For treating inflammatory processes, minimum concentration of the peroxiredoxin Prx V1hum and/or ΔPrx V1hum is determined, firstly, by proceeding from the effective concentration of peroxiredoxin Prx VI in protecting biomacromolecules from active forms of oxygen in vitro and, secondly, by proceeding from the concentration of peroxiredoxin Prx VI in healthy tissue.

Depending on the gravity of the inflammatory process and on the selected method of treatment, the concentration of peroxiredoxin Prx V1hum and/or ΔPrx V1hum in the medicament or in the pharmaceutical composition can be selected from 0.01 to 10.0 mg/ml.

For instance, in the case of injury of the respiratory organs of rat with a polysaccharide solution and in the case of a chemical burn, the empirically obtained concentration of peroxiredoxin Prx VI was 0.5-1.0 mg/ml in application of 20-50 μl of its solution directly into the trachea, which corresponded to from 10 to 50 μg of peroxiredoxin per rat. Taking into account the surface area of the rat trachea, this corresponds to the application of 5-10 μg of PrxVI peroxiredoxin per $cm^2$ of the injured tissue. This amount of peroxiredoxin VI can be used in the application to injured tissue of any mammal, including man.

In the case of using peroxiredoxin as a radioprotector, the amount of peroxiredoxin PrxVIhum or ΔPrx V1hum, introduced into the organism before the irradiation, can be selected from 1 to 10 mg/kg of the weight of animal and depends on the radiated power. In the case of sublethal dose of gamma radiation, the empirically obtained amount of peroxiredoxin was 2-5 mg/kg of the weight of animal upon injection 1 ml of the peroxiredoxin solution into the vein. This amount of peroxiredoxin can be used in the administration for any mammal, including man.

Since peroxiredoxin Prx V1hum and its fragment ΔPrx V1hum are readily soluble proteins, as solvents for carrying out application use can be made of physiological solution, Ringer solution, and other balanced salt solutions (Dawson R. M., 1986), and also other solutions based on mono- or polysaccharides, e.g., glucoses and/or vitamin-containing solvents. The same solvents can be used in preparing the composition in an air-and drop form, e.g., as a spray.

When using peroxiredoxin and/or its fragment for treating pathologies caused by bacterial flora or other factors, the effectiveness of the composition increases essentially upon adding a peroxiredoxin activator, because the reserves of the own peroxiredoxin activators in the organism are limited. Moreover, in the external administration of peroxiredoxin the activator shortage is obvious. A classical activator of peroxiredoxins is dithiothreitol (Novoselov S. V. et al., 1999). But dithiothreitol is toxic aid its use in dosage forms is ruled out. One of natural activators of peroxiredoxin VI is dihydrolipoic acid, which is non-toxic and can be prepared by restoring the S-S bond of alpha-lipoic acid (1,2-dithiolane-3-pentanoic acid) widely used in the medicine (Sang W. K. et al., 1998). Dihydrolipoic acid as the activator of peroxiredoxin is investigated in (Peshenko I. V., Shichi H., 2001) in vitro experiments. The effectiveness of dihydrolipoic acid as the peroxiredoxin activator in vivo is demonstrated in Example 8.

The concentration of dihydrolipoic acid in the composition is selected within a range of from 0.01 to 10 mg/ml, depending on the concentration of peroxiredoxin (see FIG. 11).

The use of peroxiredoxin and of its natural activator in the form of dihydrolipoic acid makes it possible to lower the concentration of the polypeptide and activator in the composition and lower the probability of origination of allergic processes in the organism.

If the inflammatory process becomes generalized (for instance, when sepsis arises) and several organs and/or systems are involved, it is recommendable to include into the formulation of the medicament antibiotics and/or glucocorticoids in combination with a composition comprising a peroxiredoxin and/or a peroxiredoxin fragment and/or dihydrolipoic acid and to carry out combined therapy.

Pharmaceutical Composition

In a general case the composition comprises an effective amount of at least one substance that comes into the group consisting of a peroxiredoxin, a peroxiredoxin fragment, dihydrolipoic acid, in combination with pharmaceutically acceptable additives in the following ratios, in weight percent:
  i) a peroxiredoxin, from 10.0 to 90.0, and pharmaceutical additives, the balance;
  ii) a peroxiredoxin and dihydrolipoic acid in total, from 10.0 to 90.0, and pharmaceutical additives, the balance, wherein the ratio of the peroxiredoxin to dihydrolipoic acid is from 1 to 50 (w/w);
  iii) a peroxiredoxin fragment, from 10.0 to 90.0 and pharmaceutical additives, the balance;
  iv) a peroxiredoxin fragment and dihydrolipoic acid, in total, from 10.0 to 90.0, and pharmaceutical additives, the balance, wherein the ratio of the peroxiredoxin to dihydrolipoic acid is from 1 to 50 (w/w);
  v) a peroxiredoxin, from 5.0 to 45.0, together with a peroxiredoxin fragment, from 5.0 to 45.0, and pharmaceutical additives, the balance;
  vi) a peroxiredoxin, from 5.0 to 45.0, a peroxiredoxin fragment, from 5.0 to 45.0, and dihydrolipoic acid, from 1.0 to 50.0, in total to 90.0, and pharmaceutical additives, the balance, where the ratio of the peroxiredoxin together with the peroxiredoxin fragment to dihydrolipoic acid is from 1 to 50 (w/w).

As pharmaceutical additives, use can be made of mono- or polysaccharides, amino acids, low-molecular proteins employed for the stabilization and subsequent freeze-drying the composition.

The pharmaceutical composition made in the form of solution for internal administration contains from 0.01 to 0.5%, preferably from 0.01 to 0.1% of the main active substance, in the form for treating wound surfaces or in the form of an ointment or suppositories for rectal or intravaginal administration contains from 0.1 to 1.0% of the main active substance, in the form of solution for eye drops contains from 0.1 to 0.3% of the main active substance.

For preparing liquid media, a solvent is used, selected from the group: a) a balanced salt solution, b) a balanced salt solution and a peroxiredoxin activator in a concentration from 0.001% to 1.0% (w/w).

For preparing lyophilized forms, mono- and/or polysaccharides are used, which are known for stabilizing biologically active polypeptides for pharmacology. Lyophilized forms can be used for preparing powders selected from the group: a powder for preparing injection, infusion solutions, a powder for inhalations, a powder for use in ointments, gels, suspensions, a powder for preparing tabletted forms.

The concentration of peroxiredoxin in the formulation of a powder is from 0.1% to 90%. In the tabletted form to be used sublingually, the peroxiredoxin concentration can be from 0.01% to 1.0%.

A multimodality therapy can be used, when the composition comprising a peroxiredoxin and/or a peroxiredoxin fragment and/or an activator is administered jointly with or after the application of at least one broad-spectrum therapeutic agent.

The therapeutic agent is selected from the group consisting of: i) antibacterial, antivirus, antifungal, antihistaminic preparations, ii) high-molecular enzymes which provide additional protection against free radicals (superoxide dismutase, catalase, glutathione peroxidase), iii) low-molecular compounds which provide additional lowering of the level of free radicals inside the cell (tocopherol, glutathione, ubiquinone), iv) preparations used for the transplantation or cryopreservation of organs, v) biologically active proteins, e.g., insulin, vi) hormones, vii) vitamins, viii) cytokines.

The therapeutic agent used jointly with peroxiredoxin must not inhibit the biological activity of the peroxiredoxin as an enzyme.

The cited forms of the composition and the methods of using thereof do not limit other variants known from the field of medicine or veterinary, when using antioxidant therapy. Variations which follow from the present invention and are obvious to any specialist of average skill in the art must be considered within the framework of the proposed invention.

Materials and Methods for Producing Peroxiredoxin and Fragment Thereof

For checking the effectiveness of the composition and for elucidating the properties of the natural and recombinant peroxiredoxins, a method of isolating natural protein from the organs of mammals was used (Pesenko I. V. et al., 1998), or a recombinant protein and/or its fragment was obtained by using a prokaryotic expression system (Merkulova et al., 2002). Methods of preparing recombinant peroxiredoxin Prx V1hum and its fragment ΔPrx V1hum are considered as examples which include but do not limit the use of other types of peroxiredoxins.

EXAMPLE 1

Preparing Natural Peroxiredoxin of Rat Prx V1rat

Natural Prx VIrat was prepared according to the following procedure. Peroxiredoxin Prtx VIrat was isolated from the olfactory epithelium of a Wistar line rat, which contains maximum amount of this protein. The isolated olfactory epithelium was washed twice in a physiological solution and homogenized therein. The homogenate was centrifugated for 5 min at 500 g, the supernatant was again centrifugated twice at 20000 g and dialyzed for 12 hours against solution A whose formulation comprises: 12 mM of Tris/HCl, pH 7.8, 1 mM of $MgCl_2$, 1 mM of dithiothreitol. After the dialysis the extract was applied to a chromatographic column (305×12.5 mm)

filled with DEAE-Sepharose gel (DEAE-Sepharose, Pharmacia) and preliminarily balanced with solution A. Proteins were eluted with linear variation of NaCl gradient from 0 mM to 500 mM in solution A at 17° C. The volume of the solution was 750 ml, the elution rate was 0.7 ml/min. The fractions were analyzed for antioxidant activity. The fractions containing Prx VIrat were concentrated and then chromatographed on a column filled with Sephacryl S-200 gel (820×16 mm). The column was eluted with buffer B: 25 mM of Tris/HCl, pH 7.8, 100 mM of NaCl, 1 mM of MgCl$_2$, 1 mM of dithiothreitol. The elution rate was 0.6 ml/min, at t° 4° C. The fractions containing Prx VIrat were collected, concentrated, dialyzed against physiological solution, and used in subsequent experiments. The primary structure of rat Prx VI (Andreeva S. G. et al., 1998) contains 223 amino acids with a calculated molecular mass of 24630 Da. (EMBL/GenBank, Y17295).

EXAMPLE 2

Constructing Recombinant Plasmid DNA pET23-a(+)Prx V1hum, Encoding Full-Sized Prx V1hum Complementary DNA encoding human peroxiredoxin Prx V1hum (SEQ ID NO: 1) was isolated from clone HA0683 (Nagase T. et al., 1995, GenBank, D14662) by the method of polymerase chain reaction (PCR) (Taylor G., 1994), with the use as primers oligonucleotides, in whose sequences point replacements are made for corresponding restriction sites to be created. As a direct primer use is made of the sequence 5'-ATCACCCGTCCATATGCCCGGAGG-3' (SEQ ID NO: 3) (the NdeI restrictase recognition site is underlined), as a reverse primer use is made of the sequence 5'-CCA GAATTCTTAAGGCTGGGGTGTG-3' (SEQ ID NO: 4) (the EcoRI restrictase recognition site is underlined).

The reaction mixture for carrying out PCR contains (in the volume of 50 μl): 1 nl of plasmid DNA, 20 nmole of each primer, 5 μl of a 10-fold buffer for CPR (Promega Corporation), 200 μM of each dNTP, 5 units of Taq-polymerase. The reaction is started with the stage of preliminary DNA denaturation—94° C. for 5 min, then 30 PCR cycles are carried out with the following parameters of the temperature cycle: denaturation—30 seconds at 94° C., annealing with the primers—30 s at 60° C., elongation—45 s at 72° C. with subsequent incubation at 72° C. for 5 min. After treating the reaction product with the corresponding restrictases, peroxiredoxin cDNA is cloned into plasmid pET23-a(+) along the NdeI-EcoRI restriction sites, with the help of restriction enzymes of MBI Fertmentas (Studier, F. W., Moffatt, B. A., 1986). The physical map of recombinant plasmid pET-a(+)Prx V1hum is shown in FIG. 1.

EXAMPLE 3

Constructing Recombinant Plasmid DNA pET23-a(+)ΔPrx V1hum, encoding N-terminal fragment of human Prx VI The initial plasmid for constructing new sequences of DNA fragments encoding polypeptide fragments ΔPrx V1hum is the plasmid pET23-a.(+)Prx Vlhum determining the expression of full-size recombinant Prx Vlhum, which is used as a matrix for PCR. As one of the variants of a short DNA fragment, the N-terminal fragment ΔPrxVI is selected, having a length of 177 a.b. (SEQ ID NO: 2). As the direct primer use is made of the sequence 5'-GCGAAATTAATAC-GACTCACTATAGGG-3' (SEQ ID NO: 5) (complementary to the promoter region of the vector pET23-a(+)ΔPrx V1hum). As the reverse primer use is made of the sequence 5'-CCATCCTTCGAATTCAACTTAGGTGGC-3' (SEQ ID NO: 6) (the EcoRI restrictases site is underlined).

The reaction mixture contains (in the volume of 50 μl): 1 ng of plasmid DNA, 20 pmole of each primer, 5 μl of the buffer for CPR (Promega USA), 200 μM of each dNTP, 5 units of Taq-polymerase. The reaction is started with preliminary DNA denaturation—94° C. for 3 min, then 10 PCR cycles are carried out with the following parameters of the temperature cycle: denaturation—30 s at 94° C., annealing with the primers—30 s at 62° C., elongation—45 s at 72° C. with subsequent incubation at 72° C. for 5 min. After treating with the corresponding restrictases, the ΔPrx V1hum fragment is ligated with the NdeI-EcoRI fragment of the plasmid pET-a (+), using the DNA ligase of the phage T4. The accuracy of assembling the construct is assessed by the restriction analysis of and sequencing the obtained insert according the modified method of Sanger (Sanger F. et al., 1997). The physical map of the recombinant plasmid pET-a(+)ΔPrx V1hum is shown in FIG. 2

EXAMPLE 4

Expressing Peroxiredoxin Prx V1hum cDNA and ΔPrx V1hum DNA Fragment in *E.coli* Strain For the expression of cDNA fragments of peroxiredoxin Prx V1hum or of peroxiredoxin ΔPrx Vlhum, the strain of *E.coli* BL-21(DE-3), which carries in the chromosome a bacteriophage T7 RNA gene under control of inducible lac-promoter (Studiuer F. W., Moffatt B. A., 1986), is selected as the host strain.

The transformation of competent cells of *E.coli* BL-21 (DE-3) is carried out by the chemical method with the use of calcium chloride (Sambrook J. et al., 1989). The obtained strain of *E.coli* BL21/DE3/pET23-a-Prx V1hum for producing the full-size peroxiredoxin and the strain of *E.coli* BL21/DE3/pET23-a(+)ΔPrx V1hum for producing the peroxiredoxin fragrnent are characterized by the following main features. Morphological features: the cells are small, rod-like, gram-negative, non-sporiferous, 1×3.5 μm, mobile. Cultural features: the colonies grown on the agarized medium LB are smooth, semi-transparent, glossy, gray. The edge is even, the diameter of the colonies is 1 to 3 mm, the consistency is paste-like. The growth in the liquid media (LB, minimum medium with glucose) is characterized by uniform opacity, easy sedimentation. Physico-biological features: the cells grow at 4-42° C., optimal pH is 6.8-7.6. As the source of nitrogen use is made of both nitrogen salts and of organic compounds: amino acids, peptone, Trypton, yeast extract. As the source of carbon when growing on the minimal medium, use is made of glycerin, carbohydrates, amino acids. Resistance to antibiotics: the cells of the producing strain display resistance to ampicillin (to 300 mg/ml), conditioned by the presence of β-lactamase gene (bla) in the plasmid.

For producing recombinant protein of peroxiredoxin Prx V1hum or of peroxiredoxin Prx Vlhum, cells are grown at 37° C. till the absorption value $A_{600}$ of 0.6 is reached in the liquid culture. Then for inducing expression of the proteins the IPTG lac-inducing factor is added to the final concentration of 0.4 mM, and the incubation is continued for another 4-5 hrs. After that the cell suspension is subjected to centrifugation at 4000 g for 20 min at 4° C. The precipitate, containing cells of the producing strain, is destroyed ultrasonically and centrifugated again. The protein fraction containing the target product is settled out with a saturated solution of $(NH_4)_2SO_4$ and dialyzed against 12 mM of Tris-HCl buffer (pH 7.8), whose formulation comprises 1 mM of $MgCl_2$ and 1 mM of DTT. The protein mixture is chromatographed on DEAE-sepharose in the sodium chloride gradient. The fractions containing the target polypeptide are subjected to further purification with the aid of gel-filtration on Sephacryl-200 and analyzed by polyacrylamide gel electrophoresis in the presence of sodium dodecyl sulfate.

EXAMPLE 5

Determination of the Productivity of the ΔPrx VI Producer Strain

An individual colony of *E.coli* BL21/DE3 containing constructed plasmid pET23-a(+)ΔPrx V1hum is introduced into 5 ml of liquid medium LB containing 100 μg/ml of ampicillin. The colony is grown at 37° C. on a rocker at 180 rpm for 2.5 hrs, till the absorption value $A_{600}$ of 0.6 is reached in the liquid culture. Then IPTG is added to the 0.4 mM concentration and the incubation is continued under the same conditions for 6 hrs. A 1 ml sample is taken and centrifugated at 6000 rpm, after that cells are suspended in 100 μl of a buffer containing 125 mM of Tris-HCl (pH 6.8), 20% of glycerin, 3% of sodium dodecyl sulfate and 0.01% of bromophenol blue. The cell suspension is warmed up for 10 min on a boiling water bath. 2.5 μl, 5 μl, 7.5 μl, 10 μl, and 15 μl samples are taken and analyzed by electrophoresis in a 15% acrylamide gel containing 0.1% of sodium dodecyl sulfate (Laermli U. K., 1970). The gel is stained with Coomassie R-250 and scanned on an Ultrascan XL laser densitometer. According to the scanning data, the polypeptide ΔPrx V1hum accounted for 30% of the total cell protein, this corresponding to the yield of fin al pure protein product of 30 mg/l of the cell culture.

Properties of Natural, Recombinant Peroxiredoxin and of Its Fragment

EXAMPLE 6

Comparison of the protector properties of recombinant full-size Prx Vlhum with the protector properties of natural rat Prx VIrat and with the protector properties of N-terminal ΔPrx V1hum in terms of protecting glutamine synthetase of *E.coli* from inactivation in a model oxidative system in vitro.

For determining the activity of different types of peroxiredoxins, their ability to protect glutamine synthetase from the $DTT/Fe^{+3}/O_2$ oxidative system is measured. Glutamine synthetase is isolated from cells of the *E.coli* DH5α strain (Streicher S. L., Tyler B., 1980) and inactivated in the presence of a $Fe^{3+}/O_2$ oxidative system and a peroxiredoxin activator—in the model oxidative system generating free radicals (Kim K. et al., 1988). A 60 μl volume incubation mixture is used, which contains 5 μg of glutamine synthetase, 3 mM of an activator, 3 μM of $Fe^{3+}$, 50 mM of HEPES, pH 7.3, incubated for 10 min at 37° C. As the activator of natural rat Prx VIrat DTT is used. As the activator of recombinant Prx Vlhum dihydrolipoic acid is used. The residual activity of glutamine synthetase is assessed by adding to the sample 200 μl of a reaction mixture which comprises: ADP, 0.4 mM; glutamine, 150 mM; K—$AsO_4$, 10 mM; $NH_2OH$, 20 mM; $MnCl_2$, 0.4 mM; HEPES, 100 mM, pH 7.4. After incubation for 10 min at 37° C., 100 μl of a stain is added to the sample. The stain formulation includes: 5.5 g of $FeCl_3.6H_2O$, 2 g of TCA, 2.1 ml of concentrated HCl (38%) per 100 ml of $H_2O$. The protector properties of peroxiredoxin for protecting glutamine synthetase of *E.coli* from inactivation are determined as the ratio of the remaining activity of the enzyme after the inactivation in the presence of different concentrations of peroxiredoxin to the activity of non-inactivated glutamine synthetase. The results of tests show that the recombinant full-size Prx Vlhum has antioxidant characteristics close to the natural rat peroxiredoxin Prx VIrat. In its turn, the N-terminal fragment ΔPrx V1hum has antioxidant characteristics close to the recombinant full-size Prx Vlhum (see FIG. 3).

EXAMPLE 7

Determination of the Cytotoxicity of Peroxiredoxins

The cytotoxicity is determined from the influence of recombinant Prx V1hum or of natural rat Prx V1rat on the level of proliferation of line L929 human lymphoblastoma cells and of T-lymphocytes from the spleen of line NRRI rats stimulated with concavalin A.

Cells of two lines with the concentration of $10^4$ cells/ml medium were cultivated in RPMI 1640 containing 5% of bovine fetal serum. The stimulation of T-lymphocytes was carried out with the 0.1 μg/ml concentration of concavalin. In the case of T-lymphocytes the proliferation level was determined from the inclusion of $^3H$-thymidine. The number of live line L929 cells was determined in a 96-cell plate with the aid of a Trypan stain, followed by scanning on a Multiscan multichannel photometer (LKB, Sweden).

Natural Prx V1rat and recombinant Prx V1hum peroxiredoxins (in 0.1-10 μg/ml concentration) did not produce any effect on the number of live line L929 cells (see FIG. 4). In the case of T-lymphocytes stimulated with concavalin A, the cell proliferation level increased approximately twofold in the presence of natural or recombinant Prx V1hum (in 0.1-1.0 mg/ml concentration) as against cells simply stimulated with concavalin A.

EXAMPLE 8

Comparative Characteristics of Peroxiredoxin Activators

For determining the effectiveness of peroxiredoxin activation with dithiothreitol or with dihydrolipoic acid (natural activator), use is made of the ability of peroxiredoxin to protect glutamine synthetase from inactivation caused by the metal-catalyzed oxidative system.

A 60 μl volume incubation mixture which contained 5 μg of glutamine synthetase, 50 μg peroxiredoxin VI, 3 mM of an activator, 3 μM of $Fe^{3+}$, 50 mM of HEPES, pH 7.3, and dithiothereitol or dihydrolipoic acid of different concentrations, was incubated for 10 min at 37° C. The residual activity of glutamine synthetase is assessed by adding to the sample 200 μl of a reaction mixture (ADP, 0.4 mM; glutamine, 150 mM; K-$AsO_4$, 10 mM; $NH_2OH$, 20 mM; $MnCl_2$, 0.4 mM; HEPES, 100 mM, pH 7.4). After incubation for 10 min at 37° C., 100 μl of a stain was added to the sample. The stain formulation includes: 5.5 g of $FeCl_3.6H_2O$, 2 g of TCA, 2.1 ml of concentrated HCl (38%) per 100 ml of $H_2O$. The degree of the peroxiredoxin activity was determined from the protein concentration value, at which 50% preservation of the glutamine synthetase activity was observed.

The degree of glutamine synthetase protection in the function of the concentration of thiols is shown in FIG. 11. As is seen from the plots, the antioxidant effectiveness of dihydrolipoic acid is almost equal to dithiothreitol and substantially surpasses the effectiveness of lipoic acid.

EXAMPLE 9

Distribution of Peroxiredoxin Prx VI in the Organism of an Animal After Injection Thereof For detecting the distribution of exogenous peroxiredoxin Prx VI in different tissues of the organism, a recombinant Prx V1hum labeled with fluorescein isocyanate was introduced into the rat's vein in an amount of 10 mg per animal. After definite periods of time the animals were sacrificed, the tissues of different organs were isolated, and luminescent analysis of the obtained samples was carried out. The obtained data showed that 15 minutes after the injection of labeled with peroxiredoxin Prx VI the latter uniformly distributes among all the organs of the rat, including the brain. The exception is bone marrow, where the amount of exogenous peroxiredoxin Prx VI was small, compared with other tissues. Thus, the method of introducing peroxiredoxin Prx VI by intravenous injection makes it possible to increase its content in almost all the tissues of the organism.

Analysis of Peroxiredoxin Properties in Investigations In Vitro and In Vivo

EXAMPLE 10

Protection of Oxyhemoglobin From the Action of Ionizing Radiation with the Aid of Peroxiredoxin Prx VI For checking the possibility of protecting biological macromolecules from destruction caused by ionizing radiation with the aid of peroxiredoxin, we have investigated the characteristics of irradiated oxyhemoglobin in control and in the presence of peroxiredoxin. In control we used a solution of oxyhemoglobin (0.16 D at 540 nm) in 0.1 M of Tris-HCl (pH 7.0) which was irradiated in a GUBE apparatus with the total exposure dose of 10 Gy. As the radioprotector peroxiredoxin Prx V1hum was used in different concentrations (5-100 µg/ml) in the presence of 50 µM of dithiothreitol. The formation of oxidized forms of oxyhemoglobin (methemoglobin) was registered at 635 nm, and aggregation of methemoglobin was registered at 700 nm.

EXAMPLE 11

Assessment of Peroxiredoxin Prx VI in Biological Samples

Polyclonal rabbit antibodies against recombinant peroxiredoxin were prepared by a standard method of double immunization of an animal with recombinant human peroxiredoxin. The titer of the resulting antibodies was 1:10000 by ELISA and 1:2000 by immunoblotting. The specificity of the antibodies was checked by immunoblotting, using a water-soluble extract of human trachea, and by immuno-histochemical methods, using paraffin sections of human lungs, which showed a high degree of specificity of the obtained antibodies.

Purified rabbit antibodies were prepared from serum by precipitation with ammonium sulfate, followed by chromatography on DEAE cellulose. Conjugates of the antibodies with cross-linked horseradish peroxidase were prepared by the conventional method of periodate oxidation according to Wilson and Nakane with the immunoglobulin/peroxidase molar ratio of 1:3.

The titer of the conjugate for human peroxiredoxin was: for ELISA, 1:1000 and for immunoblotting and immuno-histochemistry, 1:500. The specificity of the conjugate corresponded to the specificity of the serum which was used for preparing IgG.

Protocol of the enzyme immunoassay of peroxiredoxin Prx VI in biological samples:

1. 200 µl of immunoglobulin G solution are poured into the plate cells as against human recombinant peroxiredoxin (1:1000 dilution) and incubated for 30 min at room temperature.
2. The plates are washed with physiological solution (3×5 min) and blocked with 1% dry milk for 30 min at room temperature.
3. 200 µl of the samples to be investigated are poured into the plate cells and incubated for 1 hour at room temperature.
4. The plate cells are washed with physiological solution containing 0.1% Tween 40 (3×5 min).
5. 200 µl of the conjugate solution (1:500 dilution) are poured into the plate cells and incubated for 30 min at room temperature.
6. The plates are washed with physiological solution containing 0.1 % Tween 40 (3×5 min).
7. ABTS solution (25 mg of ABTS in 25 ml of citrate buffer, pH 4.0+40 µl of 3% peroxide) is poured into the plate cells.
8. The plates are scanned on a Multiscan at 405 nm.

The sensitivity of the system is tens of nanograms per milliliter of sample (Chuchalin A. G., et al., 2003).

EXAMPLE 12

Immuno-Histochemical Detection of Peroxiredoxin Prx Vi in Human Tissues

Isolated tissue was fixed in 4% formaldehyde and 0.25% glutaraldehyde on a 20 mM phosphate buffer containing 0.15 M of NaCl. Fixation was carried out for 12 hours at 37° C. The tissue was washed in physiological solution 4 times during an hour. The tissue was dehydrated by sequential routing through ethyl alcohol with increasing concentration (40-100%). The tissue was washed with a xylene-alcohol solution (1:1) for an hour, with xylene and xylene-paraffin solution (1:1) for 12 hours. The tissue was enclosed in paraffin, and 5 µm sections were produced on a microtome The sections were dewaxed with xylene and with decreasing concentrations of alcohol. Then the sections were washed with physiological solution, blocked with 5% fetal serum, the endogenous peroxidase was inhibited with 0.3% hydrogen peroxide and incubated with the conjugate for an hour, washed thrice with physiological solution and stained with diaminobenzidine (6 mg per 10 ml of 50 mM of Tris-HCl buffer, pH 7.6+200 µl of 3% hydrogen peroxide).

Therapeutic and Protector Properties of Peroxiredoxin

The specification of the proposed invention comprises particular examples of embodying thereof, which should not be construed in the context of limiting the field of using the present invention. The versions following from the present invention, obvious to any person of average skill in the given field shall be considered within the framework of the proposed invention.

EXAMPLE 13

Protector Effect of Peroxiredoxin Prx VI Injection Upon Injurious Action of Ionizing Radiation Simultaneous irradiation of all animals (Wistar line rats weighing 200 grams) was carried out on a GUBE apparatus. The exposure dose was 6 Gy. The rats were divided into two groups. The first group of the animals (n=6) was used for control. The animals of the second group (n=6) 30-60 minutes before the irradiation were administered intravenously with 1 mg of peroxiredoxin Prx VI (1 ml of physiological solution at the peroxiredoxin concentration of 1 μg/ml). After the irradiation the animals were kept in common premises with sufficient amount of food, illumination and ventilation. For histological investigation animals with symptoms of worsened general conditions were chose from each group.

The mortality data of the animals after the irradiation for different groups of the rats are listed in Table 1. As is seen from the Table, the mortality of the rats to which peroxiredoxin Prx VI was administered before the irradiation was essentially lower than in the control group. The general condition of the survived animals one year after the irradiation differed markedly in favor of the second group compared with the control group. In the animals from the first group (FIG. 5A), as compared with the animals of the second group (FIG. 5C), there is noted: a large loss in the body weight (cachexy) (the weight of 180-200 grams), scarce pilosis of the body, low motion activity, the presence of neoplastic process).

EXAMPLE 14

The Therapeutic and Protector Properties of Peroxiredoxin Prx VI in Treating the Upper Respiratory Tract of Rat After Chemical Burn The therapeutic properties of recombinant peroxiredoxin Prx VIhum in treating the upper respiratory tract of rat 24 hours after a burn were tested on a group of 4 Wistar line rats having a weight of 150-200 grams. The rats were analgized with analgin (100 mg/kg weight) and placed for 10 minutes into an exsiccator saturated with HCl vapors (the exsiccator volume was 10 liters, 20 animals were used). After the chemical burn, the rats were maintained for a definite period of time (40 min, 6 hrs, 1 day, 2 days, 14 days, 30 days), then narcotized with hexenal (300 mg/kg weight), and a sample of the tracheal epithelial tissue was isolated. For histochemical investigations the isolated sample was placed into a fixing solution containing 2% of formaldehyde and 0.5% of glutaraldehyde. The tissue was dehydrated .by sequential routing through ethyl alcohol with increasing concentration (40-100%). The tissue was embedded into LR white resin. The resin was polymerized at room temperature. 0.5 em-thick sections were made on an LKB ultratome (Sweden), using glass knives. The sections were stained with a hematoxylin-eosine and analyzed under a light microscope.

FIG. 6B shows a section of tracheal epithelium of a rat 24 hours after burn, FIG. 7B shows the same, 14 days after burn. Maximum degradation of the epithelium is observed 24 hours after the burn, the ciliated cells which provide the mucus flow in the trachea being almost absent. Two weeks later a partial restoration of the ciliated cells is observed. The application of the Prx VIhum solution is started one hour after the burn for assessing the protector effect of peroxiredoxin or 24 hours after the chemical burn during maximum degradation of the epithelium of the tracheal mucosa, for investigating the curative effect of peroxiredoxin. In the latter case the application was carried out once a day during 5 days. The rats were preliminarily narcotized by intraperitoneal administration of hexenal (70 mg/kg), the animals were fixed on an operating table, and under visual control with the aid of a binocular lens, through a catheter of 1 mm in diameter, 20 to 100 μl of peroxiredoxin solution were introduced into the trachea. The peroxiredoxin concentration was selected within a range of from 0.5 to 5.0 mg/ml. A 0.9% solution of NaCl was used as the solvent.

EXAMPLE 15

The Therapeutic Properties of Peroxiredoxin Prx VI in Treating the Upper Respiratory Tract of Rat Immediately After the Action of LPS Solution The therapeutic properties of peroxiredoxin Prx VI in treating the upper respiratory tract of rat immediately after the application of LPS were checked on a group of 4 Wistar line rats weighing 150-200 grams. The application of LPS was carried out in the following manner. The rats were anesthetized with hexenal, and 100 μl of a lipopolysaccharide solution were introduced through a catheter (the lipopolysaccharide concentration was from $10^{-9}$ to $10^{-11}$ mg/ml, the total number of the used animals was 20). After the application of the lipopolysaccharide, the rats were maintained for a definite period of time (1 hour, 3 hours, 6 hours, 7 hours, 9 hours), then narcotized with hexenal (300 mg/kg weight), and a sample of the tracheal epithelial tissue was isolated. For histochemical investigations the isolated sample was placed into a fixing solution containing 2% of formaldehyde and 0.5% of glutaraldehyde. The tissue was dehydrated by sequential routing through ethyl alcohol with increasing concentration (40-100%). The tissue was embedded into LR white resin. The resin was polymerized at room temperature. 0.5 em-thick sections were made on an LKB ultratome (Sweden), using glass knives. The sections were stained with a hematoxylin-eosine and analyzed under a light microscope.

Shown in FIG. 8C are sections of the tracheal epithelium of rat 3 hrs after the application of the lipopolysaccharide. Histological investigations showed that in the case of using LPS in concentration of $10^{-7}$ mg/animal, there were observed massive accumulation of neutrophils in the wall of the trachea, development of edema, followed by exfoliation of mucosa into the lumen of the trachea and death of cells 3 hours later.

Immuno-histological investigations showed that in many areas of tracheal epithelium already in an hour there was observed mass death of the peroxiredoxin Prx VIrat secreting cells. This led to the absence of peroxiredoxin Prx VI in the mucus covering these areas of the trachea.

For biochemical investigations we scraped the epithelium with a thin spatula, washed off the scrape with physiological solution and centrifugated at 10000 g for 15 min. The concentration of hydrogen peroxide was by the luminescence method. The dynamics of the activities of peroxiredoxin Prs VI, TNF-α and the respiratory burst of neutrophils after the application of LPS into the trachea of rat showed that maximum of the peroxiredoxin expression was observed one hour after the LPS application, while maximum of the TNF-α expression was observed in 3 hours, and the respiratory burst of neutrophils was observed 6 hours. After LPS, application of a solution of a composition based on peroxiredoxin Prx VI into the trachea was carried out. Preliminarily the rats were narcotized by intraperitoneal administration of hexenal (70 mg/kg), the animals were fixed on an operating table, and under visual control with the aid of a binocular lens, through a catheter of 1 mm in diameter, peroxiredoxin solution (20 to 100 μl) was introduced into the trachea. The peroxiredoxin concentration was from 0.5 to 5.0 mg/ml. A 0.9% solution of NaCl was used as the solvent. The application of the solution of the composition was carried out once, immediately after the application of LPS. The application of pure solvent, solutions of serum albumin (10 mg/ml) and of glutathione (10 mM) were used as control.

Histological investigation of the trachea was carried out 24 hrs after the LPS application.

Shown in FIG. 9A is a section of the tracheal epithelium of rat 24 hrs after the LPS without application of recombinant Prx VI. Shown in FIG. 9B is a section of the tracheal epithelium of rat 24 hrs after the application of LPS, followed by the application of peroxiredoxin immediately after the LPS. Complete preservation of the epithelium is observed. The only difference from intact trachea is that the number of macrophages and mast cells increased. As is seen from the photograph, almost complete preservation or restoration of the tracheal epithelium was observed.

EXAMPLE 16

Curative Properties of Peroxiredoxin Prx VI in Treating Wounds

Rats were preliminarily narcotized by intraperitoneal introduction of hexenal (70 mg/kg). The animals were fixed on an operating table, and then 2-3 mm deep and 1 cm long cuts were made in the skin of both paws with the help of a razor blade. Control cuts were irrigated with physiological solution and a bactericidal plaster was applied; in the case of using peroxiredoxin, the wound was irrigated with a solution of recombinant Prx VIhum or of its fragment ΔPrx VIhum in 0.15 M NaCl in 0.5 mg/ml concentration, and a gauze bandage soaked with the same solutions was applied. The bandages were changed once a day. The effect of the action of peroxiredoxins is shown in FIG. 10. As is seen from photographs 10B and 10C, in the case of using recombinant Prx VIhum and ΔPrx VIhum peroxiredoxins, in 5 days almost complete healing of the wound is observed as against control. Histological investigations showed that in the case of using peroxiredoxins VI the cicatrices were essentially smaller.

INDUSTRIAL APPLICABILITY

The pharmacological composition comprising at least one type of peroxiredoxin can find prophylactic and/or curative use for many diseases which are accompanied by the hyperproduction of free radicals. A higher effectiveness of the peroxiredoxin-based composition as compared with the known antioxidants makes it possible to enhance the effectiveness and shorten the terms of treatment. The pharmacological composition is not toxic and is biocompatible with the organism of mammals, including man, because the main element used in this composition is recombinant human peroxiredoxin. The low toxicity of the composition makes it possible to enhance the effectiveness of treatment owing to the simultaneous combined action on the local areas of the organism and on the organism as a whole through the agency of applications and intravenous administration of the composition. This is of particular importance when treating multifactor actions on the organism, e.g., of radiation, thermal, chemical burns, wounds, concussions originating during disasters and fires. The composition is noted for high solubility and rapid penetrability into the intracellular space of the organism, so that it is possible to treat diseases of almost all organs. The composition is compatible with any pharmaceutically suitable vehicles which do not lower the biological activity of the enzyme.

REFERENCES

1. Bauer V. and Bauer F. (1999) Reactive Oxygen Species as Mediators of Tissue Protection and Injury. Gen. Physiol. Biophys., 18, Focus Issue, 7-14.
2. Babish J. G., Howell T. Compositions containing carotenoids and tocotrienols and having synergistic antioxidant effect. PCT Appl. WO0230419 (Apr. 18, 2002)
3. Gillissen A. and Nowak D. (1998) Characterization of N-acetylcysteine and ambroxol in anti-oxidant therapy. Respir Med, 92(4):609-623.
4. Kelly F. J. (1999) Gluthathione: in defence of lung. Food Chem Toxicol, 37(9-10): 963-966.
5. Tabot O., Eliot T. Composition and method for enhancing wound healing. U.S. Pat. No. 6,187,743 (Feb. 13, 2001)
6. McLean L. R. et al. Synthetic lung surfactant having antioxidant properties. U.S. Pat. No. 5,683,982(Nov. 4, 1997)
7. White K., Kumuda C. Use of thioredoxin-like molecules for induction of MnSOD to treat oxidative damage. U.S. Pat. No. 5,985,261 (Nov. 16, 1999)
8. Davis J. M., Rosenfeld W. N., Sanders R. J. and Gonenne A. (1993) Prophylactic effects of recombinant human superoxide dismutase in neonatal lung injury. J. Appl. Physiol., 74:2234-2241.
9. Hellstrand, K. et al. Treatment and prevention of reactive oxygen metabolite-mediated cellular damage. US Patent Appl. 20010023256 (Sep. 20, 2001)
10. Vita J. A. et al. Methods of treating vascular diseases characterized by nitric oxide insufficiency. PCT Appl. WO 0135961 (May 25, 2001).
11. Chae H. Z., Robison K., Poole L. B., Church G., Storz G., and Rhee S. G. (1994) Cloning and sequencing of thiol-specific antioxidant from mammalian brain: alkyl hydroperoxide reductase and thiol-specific antioxidant define a large family of antioxidant enzymes. Proc. Natl. Acad. Sci. USA. 91:7017-7021.
12. McGonigle S., Dalton J. P., and James E. R. (1998) Peroxiredoxins: a new antioxidant family. Parasitology Today, 14:139-145.
13. Prosperi M. T., Ferbus D., Rouillard D., and Goubin G. (1993) A human cDNA corresponding to a gene over expressed during cell proliferation encodes a product sharing homology with amoebic and bacterial proteins. J. Biol. Chem. 268,11050-11056,
14. Pesenko I. V., Novoselov V. I., Evdokimov V .A., Nikolaev Ju. V., Kamzalov S. S., Shuvaeva T. M., Lipkin V. M., Fesenko E. E. (1998) Identification of a 28 kDa secretory protein from rat olfactory epithelium as a thiol-specific antioxidant. Free Rad. Biol. Med., 25, 654-659.
15. Novoselov S. V., Peshenko I. V., Popov V. V., Novoselov V. I., Bysttova M. F., Evdokimov V. A., Kamzalov S. S., Merkulova M. I., Shuvaeva T. M., Lipkin V. M., Fesenko E. E. (1999) Localization of the 28-kDa peroxiredoxin in rat epithelial tissues and its antioxidant properties. Cell. Tissue. Res. 298, 471-480.
16. Butterfield L. H.(1999) From cytoprotection to tumor suppression: the multifactorial role of peroxiredoxins. Antioxid Redox Signal Winter; 1(4):385-402.
17. Chung Y M, Yoo Y. D, Park J. K, Kim Y. T, Kim H. J. (2001) Increased expression of peroxiredoxin II confers resistance to cisplatin. Anticancer Res., March-April; 21(2A): 1129-33
18. Kinnula V. L. et al. (2002) Overexpression of peroxiredoxins I, II, III, V, and VI in malignant mesothelioma. J Pathol March; 196(3):316-323

19. Kim S. H. et al. Protein levels of human peroxiredoxin subtypes in brains of patients with Alzheimer's disease and Down syndrome. J. Neural Transm. Suppl 2001;(61):223-235.

20. Das K. C. et al. (2001) Induction of peroxiredoxin gene expression by oxygen in lungs of newborn primates. Am. J. Respir. Cell. Mol. Biol. August; 25(2):226-232.

21. Kim H. S. et al. (2002) Regulation of 1-cys peroxiredoxin expression in lung epithelial cells. Am J. Respir. Cell. Mol. Biol. August; 27(2): 227-233.

22. Fujii T. (2001) Augmented expression of peroxiredoxin VI in rat lung and kidney after birth implies an antioxidative role. Eur. J. Biochem. January; 268(2):218-225

23. Lee S. C. et al. (2000) Peroxiredoxin is ubiquitously expressed in rat skin: isotype-specific expression in the epidermis and hair follicle. J. Invest. Dermatol December; 115(6):1108-1114.

24. Park S. H. et al. (2000) Antisense of human peroxiredoxin HI enhances radiation-induced cell death. Clin. Cancer Res. December; 6(12):4915-4920.

25. Chandrashekar R., Tsuji N. Dirofilaria and brugia thioredoxin peroxidase type-2 proteins and uses thereof U.S. Pat. No. 6,352,836 (Mar. 5, 2002)

26. Novoselov V. I., Amelina S. E., Kravchenko I. N., Novoselov S. V., Sadovnikov V. B., Fesenko E. E. Application of peroxiredoxin in the healing of lung. Problems of biological and ecological safety international conference. Obolensk p. 203 (May 22-25, 2000)

27. Walker B. D., Lynn R. G. Peroxiredoxin drugs for treatment of HIV-1 infection and methods of use thereof PCT Appl. WO02077294 (Oct. 3, 2002 )

28. Andreeva S. G. et al. (1998) Structural investigations of secretory 28 kDa protein from olfactory epithelium of rat. Boorganicheskaya Khimiya vol. 24, No. 11, pp. 816-821 (in Russian).

29. Sang Won Kang, Bains I. C., Rhee S. G. (1998) Characterization of a mammalian peroxiredoxin contains one conserved cysteine. JBC, 273, 11, pp. 6303-6311.

30. Chen J. W., Dodia C., Feinstein S. I., Mahendra K. J., Fisher A. B. (2000) 1-Cys Peroxiredoxin, a bifimctional enzyme with glutathione peroxidase and phospholipase A activities. JBC, 275, 37, pp. 28421-28427.

31. Peshenko I. V., Shichi H. (2001) Oxidation of active center cysteine of bovine 1-Cys peroxiredoxin to the cysteine sulfenic acid form by peroxide and peroxynitrite. Free Radic. Biol. Med. August 1;31(3):292-303.

32. Nagase T., Miyajima N., Tanaka A., Sazuka T., Seki N., Sato S., Tabata S., Ishikawa K., Kawarabayasi Y., Kotani H., and Nomura N. (1995) Prediction of the coding sequences of unidentified human genes. DNA Res., 2, pp.37-43.

33. Knoops B., Clippe A, Bogard C., Arsalane K., Wattiez R., Hermans C., Duconseiulle E., Falmagne P., Bernard A. (1999) Cloning and characterization of AOEB166, a novel mammalian antioxidant enzyme of the peroxiredoxin family. J. Biol. Chem. 274, pp. 30451-30458.

33. Dawson R. M., Elliott D. C., Elliott W. H., Jones K. M. (1986) Data of Biochemical Research. Clarendon Press, Oxford 34. Esenaliev R. O. Radiation and nanoparticles for enhancement of drug delivery in solid tumors. U.S. Pat. No. 6,165,440 (26.12.2000)

35. Thibeault D. W., Rezaiekhaligh M., Mabry S. and Beringer T. (1991) Prevention of chronic pulmonary oxygen toxicity in young rats with liposome encapsulated catalase admisistered intratracheally: Pediatr. Puhnonol. 11:318-327.

35. Merkulova M. I., Shuvaeva T. M., Radchenko V. V., Yanin V. A., Bondar' A. A., Sofii A. D., Lipkin V. M. (2002) Human recombinant peroxiredoxin VI: producing and protector properties in vitro. Biokhimiya, vol. 67, Issue 11, pp. 1496-1501 (in Russian).

36. Studier, F. W., B. A. Moffatt, (1986) Use of bacteriophage T7 RNA polymerase to direct selective high-level expression of cloned genes, J. Mol. Biol. 189: 113-130

37. Sambrook J., Fritsch E., Maniatis T. (1989) Molecular Cloning, Cold Spring Harbor Laboratory Press, N.Y.

38. Streicher S. L., Tyler B. (1990) Purification of Glutamine Synthetase from a Variety of Bacteria. J. of Bacteriology, p. 69-78.

39. Chuchalin A. G., Novoselov V. I., Shifrrina O. N., Soodaeva S. K., Yanin V. A., Barishnikova L. M. (2003) Peroxiredoxin VI in human respiratory system. Respir. Med. February; 1997(2): 147-151.

40. Kim K, Kim I. H., Lee K. Y., Rhee S. G., Stadtman E. R. (1988) J. Boil. Chem. 263,4704-4711.

41. Laemmli U. K. (1970). Cleavage of structural proteins during the assembly of the head of bacteriophage T4, Nature, 227, p. 680-685.

42. Taylor G. (1994) In: Polymerase Chain Reaction. A Practical Approach, vol. 0.1, McPherson M. J., Quirke P., Taylor G. R. eds. Oxford Univ. Press. Oxford.

43. F. Sanger, S. Nicklen, A. R. Coulson (1997). DNA sequencing with chain -terminating inhibitors, Proc. Nat. Acad. Sci. USA, 74, p. 5463-5467.

The invention claimed is:

1. A nucleic acid molecule encoding a polypeptide, said polypeptide consisting of an N-terminal fragment DELTA of Prx VIhum including a nucleotide sequence of SEQ ID NO:4, said polypeptide having a length of 177 a.a. and having antioxidant activity which is between 80%-90% of the antioxidant characteristic of full-size Prx VIhum.

2. An expression vector comprising the nucleic acid molecule of claim 1, operationally associated with a promoter.

3. A cell comprising the expression vector of claim 2.

4. A method for producing a recombinant active N-terminal fragment of human peroxiredoxin DELTA.Prx Prx VIhum having an amino acid sequence of SEQ ID NO:4, having a length of 177 a.a., and having antioxidant activity which is close to the antioxidant characteristic of full-size PRx VIhum, which method comprises: (a) culturing the cell of claim 3 so that the active fragment of human peroxiredoxin DELTA.Prx Prx VIhum is produced by the cell in a culture; and (b) recovering the active N-terminal fragment of human peroxiredoxin DELTA.Prx.V1hum from the culture the cell, or both.

5. A pharmaceutical composition comprising, a fragment DELTA of Prx VIhum as defined in claim 1, and a dihydrolipoic acid selected from the group consisting of:
   a) fragment DELTA of Prx V1hum; and
   b) peroxiredoxin Prx V1hum and fragment DELTA of Prx V1hum and pharmaceutically acceptable additives.

6. The pharmaceutical composition according to claim 5, wherein the ratio (w/w) of human peroxiredoxin DELTA.Prx VIhum to dihydrolipoic acid is from 1:1 to 50:1.

7. The pharmaceutical composition according to claim 5, wherein the ratio (w/w) of peroxiredoxin Prx VIhum to dihydrolipoic acid is from 1:1 to 50:1.

8. The nucleic acid molecule of claim 1, wherein said encoded polypeptide has antioxidant protection of mammals from pathology-inducing exogenous and/or endogenous factors selected from the group consisting of: a) bacterial or viral infection, b) action of thermal and/or chemical factors (burn, frostbite), c) mechanical injuries (wounds, fractures, concussions), and d) exposure to ionizing and non-ionizing radiation.

9. A medicament for treatment of a human or animal from pathology-inducing exogenous and endogenous factors selected from the group consisting of: a) bacterial or viral infection, b) action of thermal and chemical factors: burn, frostbite; c) mechanical injuries: wounds, fractures, concussions; d) exposure to ionizing and non-ionizing radiation comprising peroxiredoxin PrxVI, coded by a nucleic acid molecule having a nucleotide sequence SEQ ID NO: 2 and fragment DELTA of Prx VIhum includes a nucleotide sequence SEQ ID NO: 4 as defined in claim 1.

* * * * *